(12) United States Patent
Atanasoff

(10) Patent No.: US 8,918,198 B2
(45) Date of Patent: Dec. 23, 2014

(54) METHODS AND SYSTEMS FOR CONTROL OF A SURFACE MODIFICATION PROCESS

(76) Inventor: George Atanasoff, Washington, DC (US)

( * ) Notice: Subject to any disclaimer, the term of this patent is extended or adjusted under 35 U.S.C. 154(b) by 538 days.

(21) Appl. No.: 13/144,667

(22) PCT Filed: Jan. 20, 2010

(86) PCT No.: PCT/US2010/021521
§ 371 (c)(1),
(2), (4) Date: Jul. 14, 2011

(87) PCT Pub. No.: WO2010/085496
PCT Pub. Date: Jul. 29, 2010

(65) Prior Publication Data
US 2011/0276166 A1     Nov. 10, 2011

Related U.S. Application Data

(60) Provisional application No. 61/146,143, filed on Jan. 21, 2009.

(51) Int. Cl.
| | |
|---|---|
| G06F 19/00 | (2011.01) |
| H01L 31/20 | (2006.01) |
| G05B 13/04 | (2006.01) |
| G05B 19/4097 | (2006.01) |
| G01B 11/06 | (2006.01) |
| H01L 31/18 | (2006.01) |
| H01L 31/032 | (2006.01) |

(52) U.S. Cl.
CPC ............ *G05B 19/4097* (2013.01); *H01L 31/20* (2013.01); *G05B 2219/35028* (2013.01); *G05B 13/048* (2013.01); *H01L 31/206* (2013.01); *G01B 11/0625* (2013.01); *G05B 2219/35081* (2013.01); *G01B 11/0683* (2013.01); *Y02E 10/541* (2013.01); *H01L 31/18* (2013.01); *H01L 31/0322* (2013.01)
USPC ....................................................... 700/104

(58) Field of Classification Search
CPC . G05B 19/4097; G05B 13/048; Y02E 10/541
USPC ....................................................... 700/104
See application file for complete search history.

(56) References Cited

U.S. PATENT DOCUMENTS

| | | | |
|---|---|---|---|
| 5,712,937 A * | 1/1998 | Asawa et al. ................... 385/49 |
| 6,829,559 B2 * | 12/2004 | Bultman et al. ............. 702/155 |
| 7,487,474 B2 * | 2/2009 | Ciplickas et al. ............ 716/135 |
| 2005/0042777 A1 * | 2/2005 | Boger et al. ...................... 438/8 |
| 2006/0101355 A1 * | 5/2006 | Ciplickas et al. ................. 716/2 |
| 2006/0212156 A1 * | 9/2006 | Tanaka et al. ................. 700/121 |

OTHER PUBLICATIONS

International Search Report and Written Opinion dated Mar. 22, 2010 issued in corresponding International Application No. PCT/US2010/021521.

(Continued)

*Primary Examiner* — Mohammad Ali
*Assistant Examiner* — Sivalingam Sivanesan
(74) *Attorney, Agent, or Firm* — Womble Carlyle

(57) ABSTRACT

A method and system for modifying a substrate, such a thin film, solar panel or the like detects error and/or variance and, if needed, re-optimizes the product design and/or process parameters on the fly, so that product can meet the product specification. This allows for methods and systems of process control that can adaptively change the product design in real time.

44 Claims, 14 Drawing Sheets

(56) References Cited

OTHER PUBLICATIONS

Extended European search report dated Jun. 13, 2012 issued in counterpart EP application (EP 10733815.4).

S.W. Butler et al "Application of Predictor Corrector Control to Polysilicon Gate Etching", Proceedings of the American Control Conference, Jun. 1993, pp. 3003-3007.

* cited by examiner

METHODS AND SYSTEMS FOR CONTROL OF A SURFACE MODIFICATION PROCESS

CROSS REFERENCE TO RELATED PROVISIONAL APPLICATIONS

This application claims the benefit of U.S. Provisional Patent Application No. 61/146,143, filed Jan. 21, 2009, the entirety of which is incorporated herein.

FIELD OF THE INVENTION

The present innovation generally relates to control of surface modification processes, and more particularly relates to methods and systems that can be used to facilitate error detection and real time correction of a specimen undergoing a surface modification process.

BACKGROUND OF THE INVENTION

Many surface modification processes involve addition or subtraction of a layer or material on or from a specimen based on certain design, formula, recipe or physical pattern. Surface modification is used for a variety of purposes, for example, surface modification can be used to achieve desired optical, mechanical, electrical, photovoltaic or any other physical feature that influences performance. Surface properties such as roughness, relief, chemical homogeneity, uniformity and optical, electrical, and mechanical properties can influence the properties or performance of the final device. Surface modification processes have a wide range of applications including but not limited to semiconductor fabrication, solar cells, optical thin films, nanotechnology, printing, etc.

One feature of the surface modification processes is that they typically involve repetition of the same product design or the product recipe multiple times. For example, in the printing process, all printed copies have to be the same within certain acceptable tolerances. In the manufacturing of solar cells, thin films, microelectronics, polishing, and many other processes which require surface modification it is expected that all manufactured products will be the same according to the initial product design within some accepted tolerances.

Thin film process is one example of an additive surface modification process. Thin films are thin material layers ranging from fractions of a nanometer to several micrometers in thickness. Thin films are formed (ex. by deposition) on a bare specimen or over already existing features of a device. The typical thin film deposition process takes place in vacuum conditions, which are created in a vacuum chamber. The process usually consists of creating vapors of material by chemical of physical means such as evaporation, sputtering, plasma, and subsequent condensation on the vapors on the surface of the deposited specimen or device. However, many varieties of thin film deposition processes exist, such as plating, printing, spraying, thermal diffusion, electro-chemical deposition, surface oxidation, wet deposition by spinning or dipping, formation of thin films from aqueous solutions, etc.

Thin film formation is a complex process requiring thorough control of the process parameters and in some cases, control of film characteristics, such as optical, electrical, thermal properties and mechanical stresses in the film, etc, while maintaining geometrically, stoichiometrically and structurally uniform films. Some of the materials that have been used to form thin films include amorphous silicon, crystalline silicon, oxides, nitrides, a variety of semiconductors, dielectrics, metals, polymers, inks, toners and others. Thin-films are often deposited in multiple layers to generate the specifications as desired by the manufacturer. In some cases, there is no definitive interface between separate layers as their properties gradually change from one layer to another. In other cases, the thickness and the properties of the layers are modulated, or vary in certain pre-designed ways in depth of the coating. Furthermore, the thickness and the properties of the layers can also be modulated or vary in all 2 or 3 dimensions as is the case of variety of patterned coatings, subtractive color synthesis (color printing), thin film microlenses, photonic crystals, waveguides, optical displays, and other optical products. A large variety of substrates can be used, including flexible substrates and substrates that can later be removed or etched away leaving the thin film coating to be self-supported, or to be transferred to another substrate.

One example of a subtractive surface modification process is the surface etching. Etching is used in micro-fabrication to remove layers from the surface of a specimen (e.g., a wafer) during manufacturing. Another example of subtractive surface modification process is the layer removal by laser ablation or mechanical scribing process.

Etching, scribing, and ablation are very precise processes which require very strict control of the process parameters in order to achieve the desired etching rate and selectivity. In the ion etching process, control of the ratio of ion/reactive components in the plasma offers a convenient means to control the etching rate and etching profile. Another convenient means to control the process is achieved by applying bias voltages with different magnitude, profiles, waveforms, etc.

For manufacturing of typical semiconductor elements (such as thin film transistors in display technology or semiconductor chip in microelectronics) every wafer undergoes many deposition and etching steps one after another in a pre-designed fashion. For many etch steps, part of the wafer is protected from the etchant by a "masking" material which resists etching. In some cases, the masking material is a photoresist which has been patterned using photolithography. Other situations require a more durable mask, such as patterned silicon nitride layer deposited on the wafer or over the thin film structure already deposited on the wafer. Yet, in some cases patterns are formed on the specimen by deposition of thin film through a mask located in front of the specimen in contact with the specimen (contact mask) or at a distance from the specimen (shadow mask). Examples of these are manufacturing of some thin film micro lenses, some photonic crystal structures and nanostructures.

Other examples of surface modification processes include surface grinding/polishing, implantation, ablation, printing, spraying, diffusion of material through the surface, surface wear, etc.

Most surface modification processes typically tend to "drift" over time, causing the modified surface or specimen to gradually deviate from the target values.

In the case of printing, a residual deposition of ink on the printing drums, variations in the viscosity of the printing inks, sublimation of thermoplastic resin or formation of toner particle layers on the rollers and drums in electro-photography, can cause gradual drift in the quality of the produced copies over time, and from location to location on the same sample.

In the case of surface grinding/polishing, a removal of material from the surface of the specimen and its subsequent incorporation into the polishing solution may gradually change the chemical properties of the polishing solution (such as its pH) causing formation of unwanted substances on the surface and gradual drift in the quality of the polished samples.

In the typical thin film deposition, one reason for the process to "drift" over time can be the overcoat of the processing chamber walls during the process, causing change in the thermal, optical or electrical properties inside the chamber. For example, deposition of a dielectric layer on the chamber walls during the process may gradually change the electrical conductivity and/or electro-isolation properties of the process surrounding area, the reflective properties of the walls or create temperature gradients which gradually affect the quality of the deposited specimens. In addition, there is a spatial distribution of the processing parameters inside the equipment due to geometrical or other reasons, causing non-uniformity in the plasma or gaseous phase distribution and, thus, non-uniformity of the film properties over the deposited specimen from location to location. To further complicate the situation, this spatial parameter distribution inside the processing chamber can also drift over time.

Typical example of drift in the process parameters during the process are the wear off of the sputtering target as material is removed from it, which changes the spatial distribution of the material. Another example is the decrease of evaporated material in the thermal boat as it evaporates, which may cause a gradual increase of the boat temperature and therefore, the deposition rate and the kinetic energy of the evaporated particles.

Another reason for the drift in the thin film process parameters can be the change in the temperature, pressure, current or another parameter due to the fact that the measurement sensors can change during the process. For example, deposition of material on a thermocouple changes its thermal capacity and, therefore, the temperature reading. Similar could be the situation with other sensors such as vacuum meters, gas flow meters, etc.

One example of thin film parameter drift is associated with the deposition of multi-junction solar cells. Multi junction solar cells can make better use of the solar spectrum by having multiple semiconductor layers with different band gaps. Triple junction solar cells currently in production are made of GaInP, GaAs, and Ge, which have band gaps of 1.8 eV, 1.4 eV, and 0.7 eV, respectively. In the multi junction solar cells, the different semiconductor layers are epitaxially grown directly on top of the other layers using the same substrate. As a result of this method, the lattice constant, which describes the spacing between atoms of a crystal structure, must be the same for all of the layers. A lattice mismatch small as a fraction of a percent can significantly affect the career mobility and decrease the current produced by the solar cell. Even a very small change in any of the process parameters can cause a sufficient lattice mismatch and, thus, reduce the efficiency of the final product, making it to miss its product specification.

Many modifications are made in order to partially or completely mitigate the effect of process parameters drift during the typical thin film formation processes. In some ion assisted deposition processes, the growing film is bombarded with inert or reactive ions and accelerated particles in order to supply additional kinetic energy to the surface to enhance the surface mobility of the deposited particles and thus facilitate better film growth. Another widely used solution to the problem of parameter drift is the application of different bias voltages which can modify the particle distribution during deposition or etching and enhance the formation of the film or the etched profile regardless of the other parameters' drift.

The traditional state-of-the-art process control systems and methods usually integrate over time and/or space the measured process parameter values (such as temperature, pressure, current density, bias voltage, gas flow, etc.) and try to keep them constant or within certain tolerances. In many cases, specifically in optical, semiconductor, and photovoltaic thin film processes as well as in printing, polishing, implantation, and others there is no real time monitoring of the surface under modification and decision process based on what is really taking place on the specimen. The state-of-the-art control means typically "judge" the product on a "pass/fail", step-by-step or run-to-run basis. Errors in the manufactured product are discovered too late to be corrected for the failed sample and can be corrected only for the next sample. When the products fail outside the acceptable tolerances they are rejected and the process controls are modified for the next batch of the next product. One result of this fact is that there is unavoidable percentage of rejects or final products, which are not able to meet the intended product design.

Different control schemes are devised to address the non-uniformity and parameter drift problems. Sometimes, to overcome the problem, the technologists and manufacturing engineers are forced to initially "over-design" the product to ensure that even with process drifts the final specification would still be achieved with acceptable manufacturing yield. Run-to-run control, feedback control, fault detection control and like, all intend to reduce the non-uniformity and increase the efficiency of manufacturing by measuring the outcome of the process "post factum" and correcting the process for the next sample, next run or next batch. As for the flawed sample, it is usually considered a reject or a product with inferior quality. This results in wasted materials, energy and labor and inflates the final product cost.

FIG. 1 shows a prior art state-of-art run-to-run process control, widely used in the semiconductor and other thin film manufacturing today.

From a known product specification 100 an initial design or appropriate model is chosen 101 and a series of sub-steps (recipe) is developed or generated. The recipe is loaded into the equipment control system 102 together with other additional parameters or equipment constants 103 needed to run the process such as tooling factors, calibration constants, etc. The manufacturing process starts with executing the parameters for the first manufacturing step 105. After completion of the step (or several steps one after another), the specimen can be measured/tested 106 in order to make decisions 107 about its intermediate quality by comparing it to an intermediate target 104, which is predetermined during the product design or product recipe step 101. If the intermediate target is not met within the accepted tolerance, the specimen is rejected 108 and the process parameters for the next specimen are changed 109 to correct the variance and meet the intermediate target 104 whiting the acceptable tolerance. The next decision point 110 involves a decision regarding whether all the manufacturing steps are already completed. If all steps are not completed, the specimen is sent for the next manufacturing step. After completion of all steps, a final inspection 111 is performed as to find out whether the initial product design is met. In many cases the inspection also involves comparing the product qualities with the initial specification 112. If the product design of the product specification is not met the product may be rejected or sold as inferior product 113 and the product design, model or process recipe are updated 114 in order to correct for the next product or batch of products. If the product specification is met the manufacturing process ends 115.

It is important to emphasize that the main goals of the prior art process control is typically the achievement of the initial product design within tighter tolerances. The process parameters or the recipe may change from product to product, but the initial product design/model is typically fixed at the beginning of the manufacturing process and remains static during the manufacturing. Typically there is no correction process that would correct the product design for each specimen in order to reflect its individual development during manufacturing and adaptively return it to its intended specification in case of deviation.

As a result, there is a need in the art for better methods and systems for controlling variance during surface modification processes that would allow real-time correction of the faulty specimen and its return to the intended specification. The present invention provides for real time detection of error and/or variance during surface modification processes and real time change and re-optimization of the initial product design or model in order to achieve desired product specification, for each specimen under manufacturing.

SUMMARY OF THE INVENTION

The present invention relates to the process control of surface modification processes. The surface modification processes can include, but are not limited to, thin film deposition, etching, ablation, implantation, printing, wear, material fatigue, polishing, corrosion build up and the like.

In some aspects, the present invention provides for detection of error and/or variance of one or more specimens undergoing surface modification processes and re-optimization of the product design features and the related processes parameters in order to achieve desired results according to the product specification or enhance the yield and/or productivity.

In some aspects, the present invention provides for one or more methods for control systems that would allow changing the product design "on the run" in order to achieve the desired specification.

In some aspects, the present invention provides for control systems and methods for control systems having an automatic back-loop that would allow fixing the manufacturing process on the product specification rather than on the product design by constantly adjusting the product design to ensure that the final specification will be met.

In some aspects, the present invention provides for methods and systems of process control with learning and reasoning capability that can adaptively change the process in real time.

In some embodiments, the present disclosure provides specifically for optical control of a specimen undergoing surface modification. In some examples, the disclosure provides dynamic and real-time optical control of a specimen undergoing modification.

In some aspects, the present invention provides for a computer readable medium containing software instructions which, when executed, can facilitate real-time optical control of a specimen undergoing modification.

The present invention may advantageously provide for achieving one or more of the following: a) desired specification, b) increased manufacturing yields, c) enhanced productivity, d) increased manufacturing accuracy, e) improved product efficiency, f) reduced human involvement, and g) reduced waste of materials, time, energy, labor.

The present invention can be used in the manufacture of one or more of thin films, displays, microelectronics, printing products, surface polishing products, nanostructures, photonic crystals, solar cells, among others.

In one aspect, the invention can be described with reference to the following paragraphs:

Paragraph 1—A method for detection of error or variance of one or more specimens undergoing a surface modification process and re-optimization of processes parameters or product design features to manage the error or variance of the specimen, comprising:

a. generating a design/model for a surface modification of a specimen based on a product specification;
b. generating a first modification recipe based on the design/model;
c. subjecting the specimen located in a process module to the modification using the first modification recipe;
d. measuring one or more parameters of the specimen as it is being modified using one or more sensors;
e. communicating the information about the parameters to a control module;
f. comparing the measured parameters with target parameters to determine variance;
g. calculating an updated design/model based on the variance, and
h. communicating the updated design/model to the process module by the control module, wherein the updated design/model includes information about at least one of: a new modification recipe, a required change to the design/model, a required modification to process parameters, and instructions to reject the specimens.

Paragraph 2. The method of paragraph 1, wherein the surface modification process is a thin film formation process.

Paragraph 3. The method of paragraph 1, wherein the surface modification involves at least one of thin film deposition, etching, ablation, implantation, printing, surface wear, material fatigue, surface polishing, surface diffusion and material corrosion build up.

Paragraph 4. The method of paragraph 1, wherein the specimen modification is performed to produce at least one of an optical thin film coating, semiconductor device, flat screen, solar cell and nanodevice.

Paragraph 5. The method of paragraph 1, wherein the steps 'c' onward are repeated for each round until the end of the modification process.

Paragraph 6. The method of paragraph 1, wherein the parameters are selected from one or more of transmission, or/and reflection of specified wavelength(s), thickness, polarization, refractive index, absorption, scattering, angular distribution of transmission, reflection or scattering, non-linearity, near field, photo-luminescence, electro-optical, acousto-optical and thermo-optical parameters.

Paragraph 7. The method of paragraph 1, wherein said parameter is measured by using in-situ optical monitoring system.

Paragraph 8. The method of paragraph 1, wherein said parameters are measured in real-time during the modification process.

Paragraph 9. The method of paragraph 1, wherein said parameters are measured discretely and intermittently during the modification process.

Paragraph 10. The method of paragraph 1, wherein said parameters are measured at one or more fixed wavelengths (time domain).

Paragraph 11. The method of paragraph 1, wherein said parameters are measured within one or more predetermined continuous spectral ranges (spectral domain).

Paragraph 12. The method of paragraph 1, wherein said parameters are measured simultaneously at fixed wavelengths (time domain) and within predetermined spectral ranges (spectral domain) and compared with their target values in both domains.

Paragraph 13. The method of paragraph 12, wherein the time and spectral domains are used to iteratively predict ahead of time the behavior of the specimen undergoing surface modification.

Paragraph 14. The method of paragraph 12, further comprising:

gathering and accumulating data from one or more modified specimens;

generating said models describing the behavior of the specimen, the process parameters, equipment and environment conditions and other relevant information during the modification; and using said models to refine a surface modification of subsequent specimens.

Paragraph 15. The method of paragraph 1, wherein the spatial distribution of the said parameters are measured over the entire area of the specimen.

Paragraph 16. The method of paragraph 1, wherein the said method comprises:

continuous gathering of information about processed specimens, the process parameters, equipment and environment conditions and other relevant information during modification;

creating models of process, specimen and equipment behavior during the modification; and adoption of revised models to the specimen currently undergoing modification.

Paragraph 17. The method of paragraph 16, wherein the said models are used as a learning feature to constantly improve the manufacturing process by adopting better models.

Paragraph 18. The method of paragraph 1, wherein the monitoring is conducted in real-time during the modification process.

Paragraph 19. The method of paragraph 1, wherein steps "c" onward are performed without disruption of the manufacturing process.

In another aspect, the invention can be described with reference to the following paragraphs:

Paragraph 20. A system for managing variability in production during a surface modification process, comprising:

a design module for generating a product design/model based on a product specification and generating a first process recipe based on the product design/model;

a process module to perform a surface modification of a specimen and which is operatively coupled to the design module;

one or more sensors for monitoring one or more parameters of the specimen; and a control module for comparing monitored parameters with one or more target parameters and deciding on whether to (a) continue the process to an end point, or (b) re-optimize the design model and modify the process recipe, or (c) reject the specimen;

wherein:

the control module is operatively coupled to the design module, the process module and the sensors; and the control module is enabled to receive data about monitored parameters.

Paragraph 21. A system of paragraph 20, further comprising:

an additional database module for accumulating models of process, specimen, equipment and environment behavior during the modification.

In another aspect, the invention can be described with reference to the following paragraphs:

Paragraph 22. A computer-readable medium having computer-executable instructions for control of a surface modification process which involves error detection and in real-time by performing steps of:

generating a product design/model based on a product specification;

generating a first process recipe based on the product design/model;

starting modification process of a specimen in a process chamber/module/equipment;

monitoring one or more parameters of the specimen using one or more sensors;

comparing monitored parameters with one or more target parameters; and deciding on whether to (a) continue the process to an end point, or (b) re-optimize the design model and modify the process recipe, or (c) reject the specimen.

In another aspect, the invention can be described with reference to the following paragraphs:

Paragraph 23. A method for control of a surface modification process which involves error detection and real-time correction, comprising:

generating a product design/model based on a product specification;

generating a first process recipe based on the product design/model;

starting modification process of a specimen in a process chamber/module/equipment;

monitoring one or more parameters of the specimen using one or more sensors;

comparing monitored parameters with one or more target parameters; and deciding on whether to (a) continue the process to an end point, or (b) re-optimize the design/model and modify the process recipe, or (c) reject the specimen.

Paragraph 24. The method of paragraph 23, wherein:

the surface modification process is thin film deposition.

Paragraph 25. The method of paragraph 23, further comprising:

generation of new target parameters.

Paragraph 26. The method of paragraph 23, wherein the parameters are selected from one or more from the group consisting of:

photometric, ellipsometric, near-field, scattering, photothermal, interference, diffraction, and opto-mechanical properties of the specimen.

Paragraph 27. The method of paragraph 23, wherein the sensors are optical sensors.

BRIEF DESCRIPTION OF THE DRAWINGS

Various objects, features, and advantages of the present disclosure can be more fully appreciated with reference to the following detailed description of the disclosure when considered in connection with the following figures, in which reference numerals identify like elements. The following drawings are for the purpose of illustration only and are not intended to be limiting of the disclosure, the scope of which is set forth in the claims that follow.

DETAILED DESCRIPTION OF THE PREFERRED EMBODIMENTS

Figure 1:
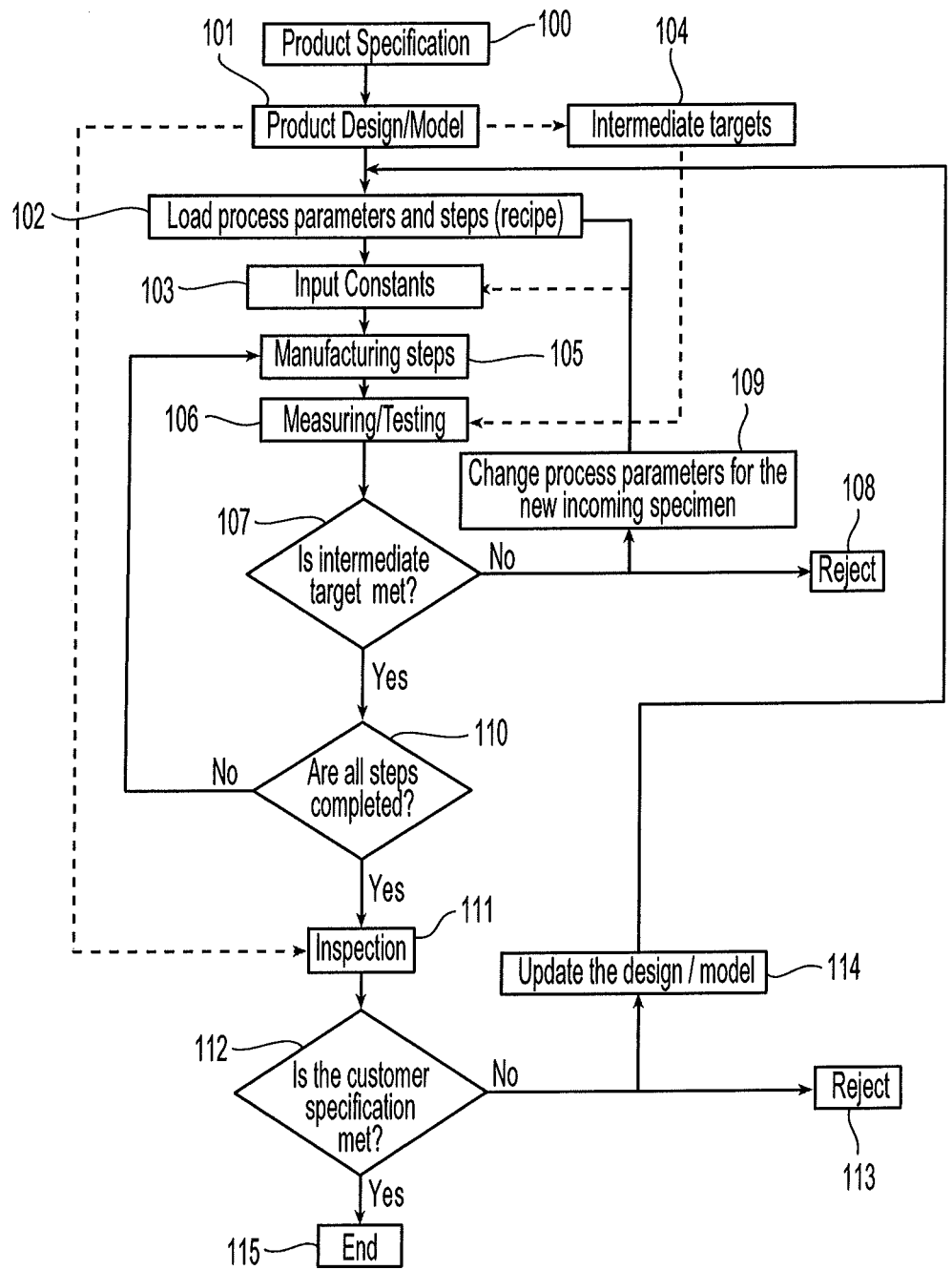
FIG. 1 is a block diagram of a prior art control process for run-to-run control.

The various aspects of the preferred embodiments are now described with reference to the annexed drawings, wherein the numerals refer to like or corresponding elements throughout. It should be understood, however, that the drawings and detailed description relating thereto are not intended to limit the claimed subject matter to the particular form disclosed. Rather, the intention is to cover all modifications, equivalents and alternatives falling within the spirit and scope of the claimed subject matter.

As used herein, the term "product specification" is intended to include the description of the necessary attributes a finished product must attain in order for the product to be used for its intended purposes.

The term "product design" refers to a specific product formula or product structure the manufacturing process is required to follow in order to attain the necessary specifications at intermittent and final step of the deposition process. An example of a product design can be a typical thin film solar cell based on superstrate process with CdTe absorber, such as Glass//160 nm $In_2O_3$:Sn/40 nm $SnO_2$/70 nm CdS/2000 nm CdTe/50 nm Cu//Encapsulant.

The term "product model" refers to a detailed product description including its design and structure but also its process parameters, setpoints, equipment and environmental conditions, data collected during real manufacturing, or even the entire history of the product from raw material to finished product. It may also take the form of a mathematical relationship. One example of product models is the typical response surface models, which are a mathematical or graphical representation of the manufacturing product response to the variations of the process variables. The models may take the form of simple polynomials in the process inputs x and be represented as a Taylor's series expansion of the true actual function about some nominal set of process input parameters:

$$y(t_j)=b_0(t_j)+b_1(t_j)x_1+b_2(t_j)x_2+\ldots b_{1,1}(t_j)x_1^2+b_{1,2}(t_j)x_1x_2+b_{2,2}(t_j)x_2^2+$$

They may also be represented as data collection in numerical, graphical or some other form.

The term "intermediate steps" are points in time during the surface modification process. For example, the product design may be specified by intermediate specifications to be achieved at a specific deposited layer, or at specific attained thickness of the layer.

The term "variance" refers to any deviation from the specified product design or product model. To a certain extent, limited variance is expected in a manufacturing environment. The accepted levels of variances are referred as allowed "tolerance."

The term "intelligent" system refers to a system having learning and reasoning abilities allowing it to predict and take independent decisions as to what measure to undertake related to process variances and errors. As an example, the intelligent feature might be implemented by the system by creating, selecting and deploying in real time most adequate models to match the ongoing specific process.

The term "seamless" refers to the ability of the control system to control and guide the manufacturing process without stopping or disturbing it by implementing its control measures, not immediately, but gradually and later in the process sequence. For example the system may detect a variance in one of the deposited layers and correct it by changing the subsequent layers in a way that the detected variance becomes part of the new solution.

The terms "time domain" and "spectral domain" refer to monitoring parameters as they change in time (such as monitoring the change in reflectance at fixed wavelength) and monitoring parameters as they change within a continuous spectral range (such as scanning a wavelength range) respectively.

The term "uniformity" refers to lacking of diversity in one or more parameter's variation (within certain limits or ranges) over at least an area of the specimen. For example a thin film may be non-uniform if its thickness or another parameter varies from position to position over the area of the sample.

The term "homogeneity" refers to lacking of structural, compositional or other parameter variation as the specimen undergoes surface modification. For example a thin film may be non-homogeneous if its chemical composition varies during deposition, and, thus, becomes different at different depth of the film.

The present disclosure provides a control system that incorporates sensors to monitor the surface properties of a product undergoing manufacturing to adaptively change the design or the used model and/or re-optimize the initial design or model to accommodate observed variances while achieving the desired product specification. Some of the applications that can benefit from the present disclosure include, but are not limited to: a) solar cell development, b) flat screen monitors, c) semi-conductors, d) optical thin films, e) nanostructured 2D and 3D devices, (f) printing, (g) surface grinding/polishing.

In some embodiments, control systems of the surface modification processes of the subject innovation can be enabled to perform production measurements in real time during surface modification process and assess for variance of the detected measurements in relation to predetermined parameters. If an error and/or variance are detected, the control system can be programmed to generate and seamlessly adapt in real time a slightly new product design or product model based on the error/variance while still achieving original product specification. Yet in some embodiments of the present innovation, at the beginning of the process, the system implements only an approximate initial product design or product model and constantly re-validates and/or improves it throughout the control process, gradually making it adequate to the ongoing process conditions on the monitored specimen. In some other examples, the subject innovation can use continuous, real-time monitoring system, which allows iterative prediction, verification and real time correction/re-optimization of a product design or a product model in order to compensate for detected errors/variance. More specifically, one embodiment of the present disclosure is directed to optical monitoring of a thin film formation on a specimen and adapting to variance in design by formulating a new product design whenever a variance above a predetermined threshold is introduced into the processes.

The description below uses thin film formation (deposition) as an example of surface modification, but persons skilled in the art would appreciate that the disclosed methods and systems can be used as control systems for several types of surface modifications processes such as etching, implantation, ablation, surface polishing, material diffusion, printing, etc., and thus, all those are within the scope of the present disclosure.

In one aspect of the disclosure, a method for detection of error or variance of one or more specimens undergoing surface modification process and re-optimization of processes parameters or design features to manage the error or variance of the specimen is described. The method involves generating a product design/product model for a surface modification of a specimen based on a product specification; generating a first modification recipe based on the product design/product model, subjecting the specimen located in a process module to the modification using the first modification recipe; measuring one or more parameters of the specimen using one or more sensors; communicating the information about the parameters to a control module; comparing the measured parameters with target parameters to determine variance; calculating an updated product design/product model based on the variance, and communicating the updated product design/product model to the process module via the control module. The updated product design/product model includes information about at least one of: a new modification recipe, a required change to the product design/product model, a required modification to process parameters, and instructions to reject the specimens.

Figure 2:
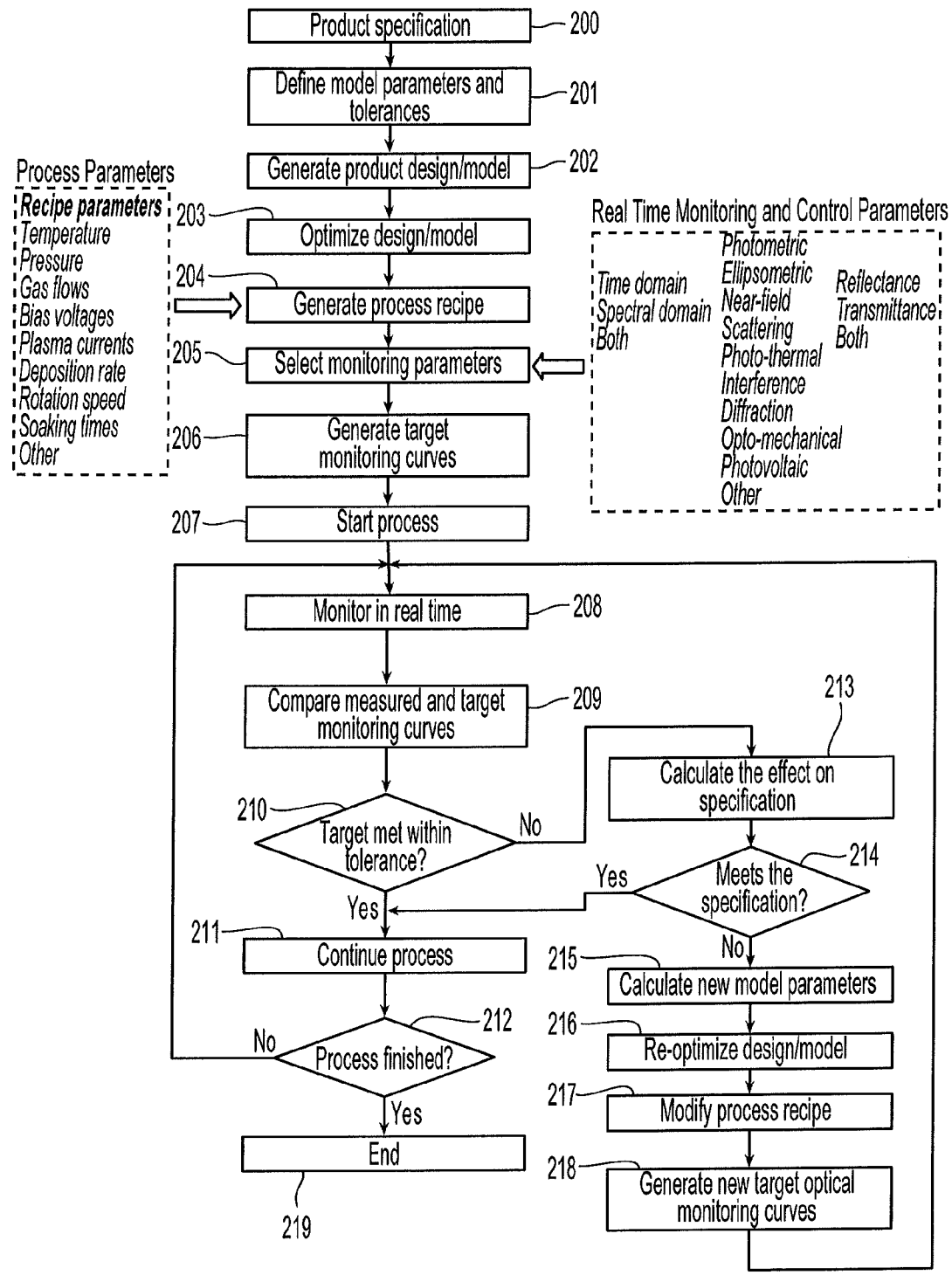
FIG. 2 is a block diagram of a method for intelligent optical control with error detection and real-time correction according to one aspect of the present disclosure.

FIG. 2 depicts one exemplary method of optical control of a specimen undergoing surface modification with error detection and real-time correction in accordance with the current invention. The correction may include real time changes made to the product design and/or the product model and subsequently related to these changes, process parameters or recipe.

Usually the method starts with a product specification 200. Based on the specification, model parameters and necessary tolerances can be defined 201 to ensure that the specification can be met. One specific non-limiting example of such a product model is a thin film copper-indium-gallium selenide (CIGS) solar cell, where the individual thin films are deposited/formed by thermal co-evaporation of materials, by co-sputtering or another process. The initial product design can be generated 202 by a computer program or can be predetermined and stored/saved unchanged for multiple runs (as is the case for solar cells, flat panel displays and other devices). In some cases a computer model can be generated, which could be a mathematical model, drawing, scheme or may take some other form.

An example of a product design can be a CIGS solar cell with the following structure: Stainless Steel//50 nm Mo/2500 nm CIGS/60 nm CdS/240 nm Al:ZnO//Glass.

The initial product design can then be optimized 203 by applying a variety of optimization techniques. This can be done using previous experience or know-how or software algorithms and computer optimization programs, which, for example, calculate the optimal thickness of the individual layers, optimize of the electric field distribution in the thin film multilayers, optimize etching profile or other parameters to ensure that all specified parameters in their combination are met within best tolerances. Some specific optimization algorithms and techniques can be applied such as linear, gradient, simplex, etc. The concept of the product design optimization will be discussed in more specific details further in this document.

From the optimized product design or product model, a complete process recipe 204 can be generated which includes a sequence of all needed process steps and process parameters such as specimen temperature, background pressure, gas flows of individual gases, bias voltages, plasma currents, deposition rates and times, speed of rotation or movement, different soaking times and intermediate parameters and many others. The recipe can be automatically loaded into the computer of a thin film equipment/module/chamber (any commercially available or known equipment can be used for the present disclosure) before the process starts. In some embodiments, the computer controlling the thin film equipment can be either different from the computer/machine used to generate the optimized recipe or it can be the same.

Next, appropriate real time monitoring parameters 205 are selected. In many cases they are already defined by the monitoring sensors and devices installed, which are part of the control system of the thin film equipment/module. For example, one may choose to measure in real time the reflectance, transmittance, or both. Using these measured parameters, one may choose to calculate and monitor in real time the optical scattering and/or its angular distributions or any combination of them from the deposited structure, the polarization components of the transmitted, reflected or scattered by the monitored sample light, near field scattering parameters or some other parameters. In some cases from the monitoring parameters some other secondary parameters can be calculated such as the film thickness, deposition rate, optical constants, material bandgap, scattering coefficients, haze, surface roughness, packing density, porosity etc. Some parameters can be monitored in time domain (their change in time), others may require monitoring their spectral change (spectral domain), while in many cases there is a need to monitor certain parameters in both domains simultaneously.

Next, target monitoring curves 206 are generated. The target monitoring curves may show the temporal and spectral evolution of the chosen monitoring parameters as they are expected to change during the film formation, starting from the bare specimen. In the case when the specimen is not moving during the deposition or performs rotational motion around one or more axes, the target monitoring curves typically evolve in time. The same monitoring spot on the specimen appears permanently or periodically in front of the monitoring sensor and the evolution of the monitored parameter is controlled constantly.

In another configuration, the target monitoring curves may be generated once for every specimen in case it performs simple translational motion. The target monitoring curves remain constant during the control process, or may slowly change as the product design or model or product recipe are corrected as a result of the real time adaptive control. This could be the case of constantly moving solar panels or flat panel displays during deposition. In this case the sensors will measure constant film properties. The differential signal between the sensors can also be monitored in order to control parameter uniformity or film homogeneity over the area of the specimen. Again, the curves can be generated in the time domain or spectral domain, or both. Monitoring simultaneously in both time and in spectral domain is particularly beneficial for thin film solar panel manufacturing.

The curves are used to compare in real time and verify the closeness of the response of the thin film being deposited to the response which is assumed by the optimized design. In many cases, each layer to be deposited or each surface to be modified is subdivided into a number of sub-layers and the performance of each of the sub-layers is calculated and generated as a target monitoring curve. In other cases, this process is performed continuously. Yet in another case, iterative prediction procedures can be deployed allowing calculating in advance the future performances and using them as intermediate targets. The comparison of the target monitoring curves with the curves acquired from the real time measurement of the specimen during the process is used to validate the correctness of the manufacturing process.

When all the needed calculations and preparations are done, the thin film manufacturing process can be started 207. The control system monitors the process in real time 208 and supplies a constant stream of data about the monitored parameters during the process.

Typically, information regarding the thin-film growth or any surface modification can be obtained from one or more sensors or monitoring devices. The sensors can be located inside or outside the thin film formation (deposition, etching, etc) chamber/module/equipment. They can be set in groups or arrays and can have both parallel and serial configurations. Sensors configured in parallel configuration can be beneficial for measuring film uniformity and homogeneity over different areas of the same specimen. The parallel configuration is also beneficial for monitoring and control of parameters on moving samples such as solar panels or flat displays, moving constantly through the manufacturing line during the surface modification. Sensors configured in serial configuration can measure the surface properties at different stages of its modification.

In some cases, the sensors can transmit the measured signal through an optical system comprising series of optical components such as lenses and mirrors, fiber optic bundles or single fibers, while the light sources, detectors and other hardware parts can be positioned outside the deposition equipment. In other cases the sensors together with the light sources, the light detectors and the other necessary components can be positioned inside the thin film deposition chamber/module and powered from outside or from inside using power batteries or some energy harvesting devices (such as photo or thermovoltaic, vibrational, inductive, etc.).

In one embodiment, the sensors can be installed inside the film formation equipment and transmit the measured data wirelessly from inside of the thin film equipment. In some embodiments, the sensors can be RFIDs, which transmit data only when initiated by an external RF reader. They can stay fixed in their position and be always focused at the same spot or the same area of a moving sample or can move during the measurement process in order to scan a larger area or to avoid blocking or shadowing the film formation area. Yet in other embodiments, the sensors can be fixed or attached directly to the monitored specimen and move together with the specimen throughout the process. Any known monitoring sensor capable of providing the desired information and withstand the environment can be employed.

The embodiments discussed herein can be implemented using a variety of monitoring devices, communication protocols and methods. For example, a continuous monitoring device may be utilized to capture real time data during the surface modification (manufacturing) process, or one may use a data capturing mechanism which provides discrete measurements rather than continuous measurements. An example of a continuous monitoring device includes an in-situ optical monitoring apparatus which may capture data in photometric or ellipsometric mode. One or more examples of an in situ optical monitoring apparatus are described in U.S. Pat. Nos. 6,879,744 and 7,345,765, whose contents are incorporated by reference. Another example is a reflectometer device with a built-in integrated sphere to capture both specular and diffusive (diffuse) reflectance. Yet another example is a near-field nanotube fiber optics sensor. Specific optical and other monitoring sensors are described in the aforementioned U.S. Pat. Nos. 6,879,744 and 7,345,765. One skilled in the art would appreciate that the above list is non-limiting.

In one example where a continuous monitoring device is utilized, data is captured in real time, preferably with an in-situ optical monitoring device, which can feed the data to the control system to verify deviations from the original product design. The most typical way to capture information from the specimen is to send one or more light beams to the monitoring area and capture the reflected or transmitted signal. This is done by deploying one or more light sources such as white light sources, LED sources, broadband light sources, lasers, etc. and, respectively, light detectors such as silicon, germanium, InGaAs, PbS as well as certain positioning light detectors, detector arrays and matrices, etc. The detector can be part of a spectrally dispersive device such as a monochromator, spectrometer, optical spectrum analyzer, etc or can be a standing alone component. The signal from the detectors is converted into a digital signal by using the driver of the device or by using an external analog-digital converter.

The monitoring parameter data received by the system during the in-situ process monitoring are used to calculate the performance of the thin film or other layered structure under formation (monitored performance). The monitored performance includes the corresponding target performance real optical monitoring curves, showing the evolution in the spectral, diffractive, photovoltaic or another performance of the surface formation as it changes during deposition starting from the initial specimen.

If the monitoring sensor(s) monitor the spectral reflectance in the time domain (at a fixed wavelength), the time domain curve might be re-calculated in the spectral domain to show how the spectral distribution of the parameter is changing during the deposition. The monitored performance in both domains is then compared in real time with the target performance to verify that they match within the acceptable tolerances 209.

The comparison of the curves is followed by a decision point 210, when the system decides whether the target performance is met at this intermittent stage. In case the curves correspond to each other, the system verifies whether the process is finished or has to continue 211. In case the process is finished 212, the system issues a message that the product is finished and the process has ended 219, or, otherwise, continues the process.

If the target performance is not met within the specified tolerance, the system calculates/predicts 213 ahead in time the final performance of the product, assuming that the new measured parameters are going to be in place until the end of the process. The calculated final performance is compared to the product specification 214. If the product specification is going to be met within the tolerances, no action is needed and the process continues. However, if the product specification is not going to be met, the system uses the measured deviation to calculate new product design or product model parameters 215 which take into account the current state of the specimen, and which, if followed, are able to return the product to its intended product specification.

Next, the product design 216 is re-optimized to accommodate the measured deviation and change the design. As a result some process parameters might also require some change 217. In a similar fashion re-optimization 216 may take place in two forms: in a continuous manner or in a discrete manner. Re-optimization 216 may include modification of the original (initial) design or model, modification of production/process parameters, or combinations of the above.

In the continuous re-optimization, the calculation occurs during the deposition process itself. However, this may be limited by the type of monitoring system utilized, since re-optimization will occur only upon detection of a variance, which may be fed continuously or intermittently by the monitoring device. Re-optimization in a similar fashion may be designed to occur only at discrete points in the deposition process.

In one or more embodiments, the method works in conjunction with the currently existing process controls and systems, that may be already installed or part of the equipment, and tries to interfere with them as little as possible. The proposed method offers an additional level of process control, which can complement the traditional control methods. For example, the corrected product design may require slightly different film thickness of some individual layers and, therefore some deposition times have to be re-adjusted. If this is the case, then the control system has to communicate with the traditional control system. However, in many cases, a control system in accordance with the present invention searches for a soft solution, which would not require any immediate change and would not disturb or disrupt the ongoing process (seamless operation).

Prior art control methods and systems keep all the parameters constant during one manufacturing step and change them only for the next sample (sample-to-sample control) or next run (run-to-run control). In contrast, a control method and system in accordance with some embodiments of the present invention, monitor in real time the optical parameters of the sample during manufacture and may change the deposition time of the layer under deposition or the layers that remain to be deposited. In this way, one may correct for minor process parameter drift, which remains unnoticed or uncontrolled by the prior art control method and system and automatically guides the product, keeping it focused on its product specification.

Yet, in another embodiment, the proposed control system may change some process parameters in order to compensate for the drift. For example, it may change some bias voltage during etching, change the distance between the shadow mask and the specimen, or change reactive gas mixture during plasma process.

Furthermore, in other embodiments, the control method and system can be designed not to automatically change any process parameter, but instead issue a message which requires acknowledgement by an operator or control system. The control method/system, in turn, utilizes the measured data to devise a new optimal design to meet specifications in one of the following ways:
 (1) Re-optimize in real-time at the first detection of a deviation; or.
 (2) Re-optimize at the completion of one layer and prior to the commencement of forming the next layer.

In contrast to prior art approaches, the second way requires real time simulation in advance and comparison to the product specification and re-design of the upcoming layers in order to meet the specification. The preference of which methodology is better suited will depend on the individual application. After the product design is changed, the system generates new target optical monitoring curves 218 corresponding to the new deign. These curves are fed back and the process continues following the corrected curves.

In another aspect, the present invention is directed to a method for control of a surface modification process which involves error detection and real-time correction, and entails: generating a product design or product model based on a product specification; generating a first process recipe based on the product design or product model; starting modification process of a specimen in a process chamber/module/equipment; monitoring one or more parameters of the specimen using one or more sensors; comparing monitored parameters with one or more target parameters; and deciding on whether to continue the process to an end point or re-optimize the design or model and modify the process recipe or to reject the specimen.

In another aspect, the present invention is directed to a method of control of surface modification/thin film deposition process which includes: providing a first deposition recipe; depositing a layer onto a specimen (wafer) using a first deposition recipe; measuring one or more properties of the deposited layer; comparing the measured property of the deposited layer with the deposition model to determine variance, if any; and generation, if needed, of a revised recipe based upon the variance.

In yet another aspect, the present invention is directed to a method of control of surface modification/thin film deposition process which includes: generating an initial product design and developing a production recipe based on a product specification, and the status of manufacturing equipment and/or other information. In this aspect, the system can perform most of the design, manufacturing, adaptive control and other operations without human involvement.

In yet another aspect, the present invention is directed to a method of control of surface modification/thin film deposition process which includes: the generation of initial product design and/or production recipe which are only first approximation or rough models of the product to be manufactured and the manufacturing process. As the surface modification process starts, the initial design and production recipe are constantly modified and validated according to the real time information about the product being manufactured and become more and more accurate as the production process progresses. In such case, the only information needed to manufacture a thin film product is the product specification. All other needed information is generated by the system itself, maintained in the system database or collected/extracted by the system from other databases. In the example of the solar cell Stainless Steel//Mo/CIGS/CdS/Al:ZnO//Glass, the initial product design may include only the substrate type (in this case stainless steel) and the thickness of the Mo layer. As the deposition of CIGS layer starts, the system measures in real time the real physical parameters of the film and uses the information to specify the design of the remaining part of the cell. For example, as the CIGS layer starts being deposited, the system measures the optical scattering and calculates the surface roughness of the absorber and calculates ahead of time what physical thickness will be sufficient to achieve the specified photovoltaic properties. Therefore, the design parameters of the layers may vary from sample to sample in order to reflect the real conditions on the surface of the sample.

In another aspect, the present invention is directed to a system for managing variability in production during a surface modification system which includes: a design module for generating a product design/model based on a product specification and generating a first process recipe based on the product design/model; a process module to perform a surface modification of a specimen, the process module being operatively coupled to the design module; one or more sensors for monitoring one or more parameters of the specimen; a control module for comparing monitored parameters with one or more target parameters and deciding on whether to continue the process to an end point or re-optimize the design model and modify the process recipe or to reject the specimen. The control module is operatively coupled to the design module, the process module and the sensors; wherein the control module is enabled to receive data about monitored parameters. In some embodiments of the disclosure, the different modules can be incorporated into a single computing unit or can reside in different computing units. The systems described here can be operated as described above to implement real-time or adaptive control of surface modification processes. One skilled in the art would appreciate that the number of modules and the combinations can be varied while achieving the advantages of the present disclosure.

In another aspect, an additional database module is included into the system, which constantly accumulates designs, models, recipes, product histories, equipment conditions and other information about many previously manufactured products and manufacturing cycles. This module is used by the system to extract already recorded solutions to ongoing problems from previous histories and save calculation and optimization time. Yet, in another disclosure the database module is used to provide a learning/reasoning capability to the control system, where the system constantly searches for most adequate designs, models, recipes and product histories for previous products and implements them in real time for the current product under manufacturing.

All the above methods/systems can be automated or codified into a software application using skills known in the art. The software codification can be performed using any of the computer recognizable languages or codes. The software application can be part of the thin film equipment or can reside on a distinct machinery/computer. The software can be programmed to interact with one or more modules such as a control module, process module, design module or database module. The above methods can also be implemented through a computer/machine readable medium.

Figure 3A:
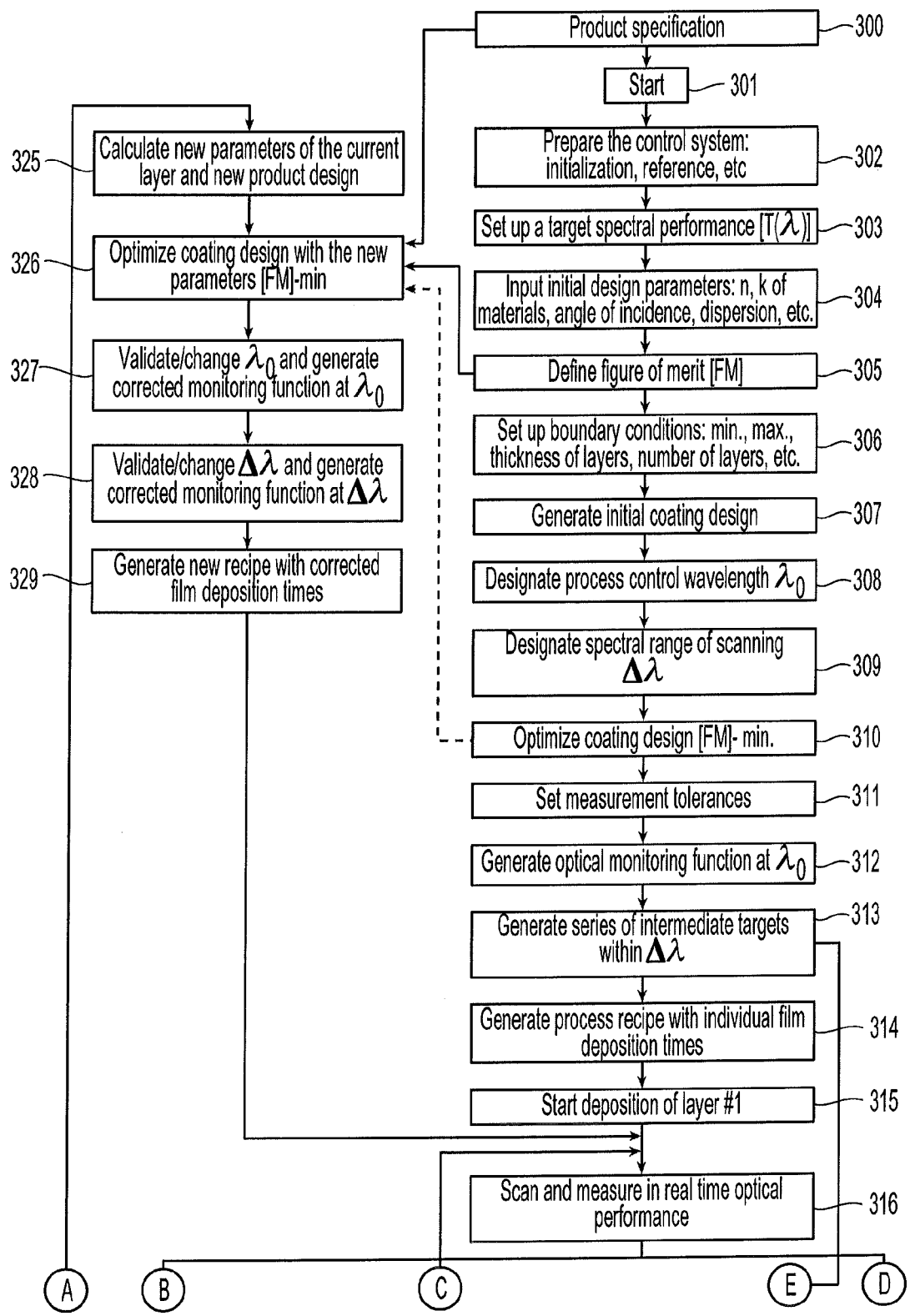
FIG. 3 is a flowchart providing an overview of a calculation algorithm that adaptively modifies design to meet specification of a specimen undergoing thin film deposition according to one aspect of the present disclosure.
Figure 3B:
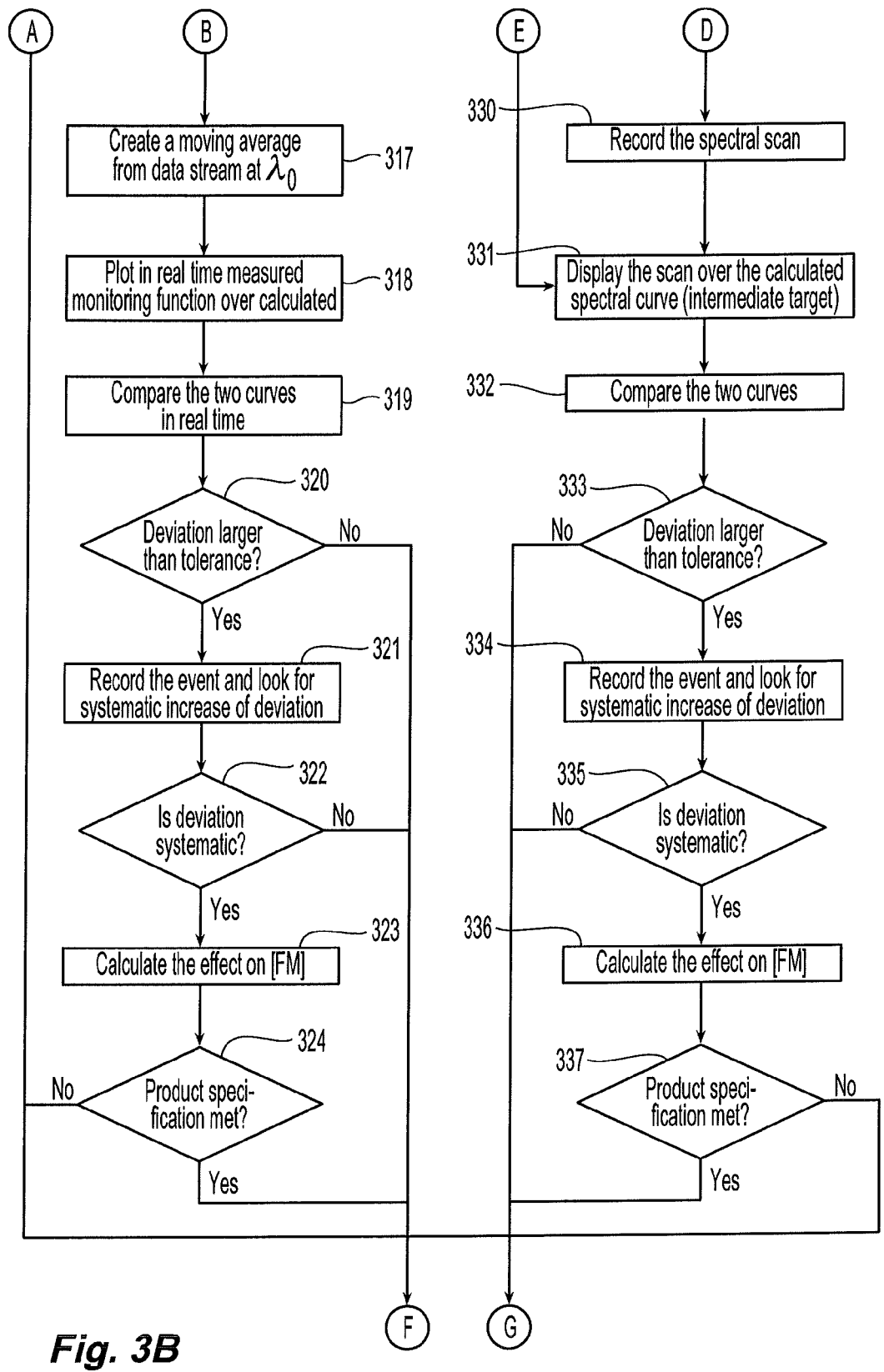
Figure 3C:
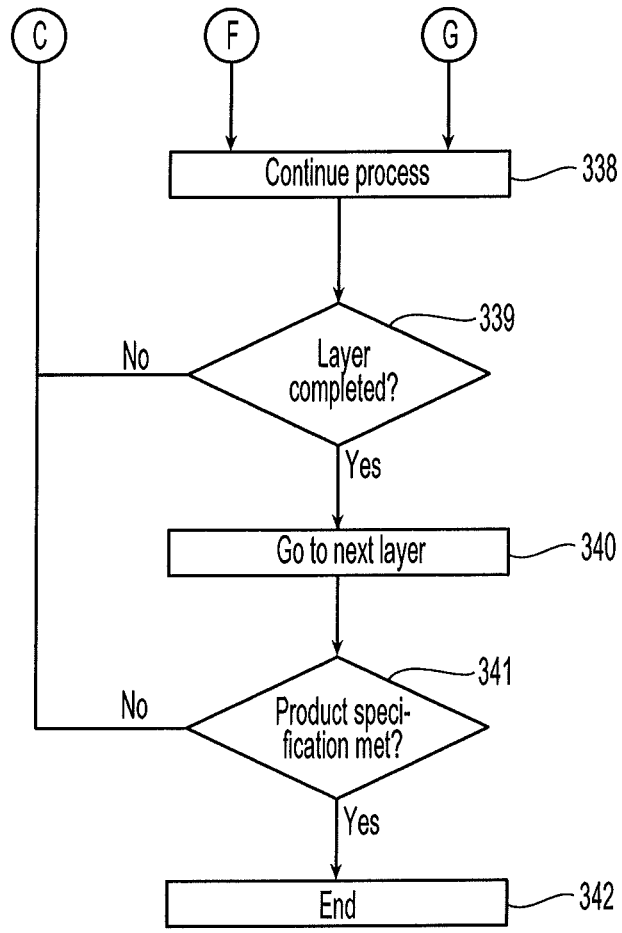

In one aspect of the disclosure, as depicted in FIG. 3, a calculation algorithm that adaptively modifies the design to meet specification of a specimen undergoing thin film deposition is provided. The algorithm involves the following:

1. The process starts with having a product specification 300 which may contain the required specific functional features of the final product.

Figure 4:
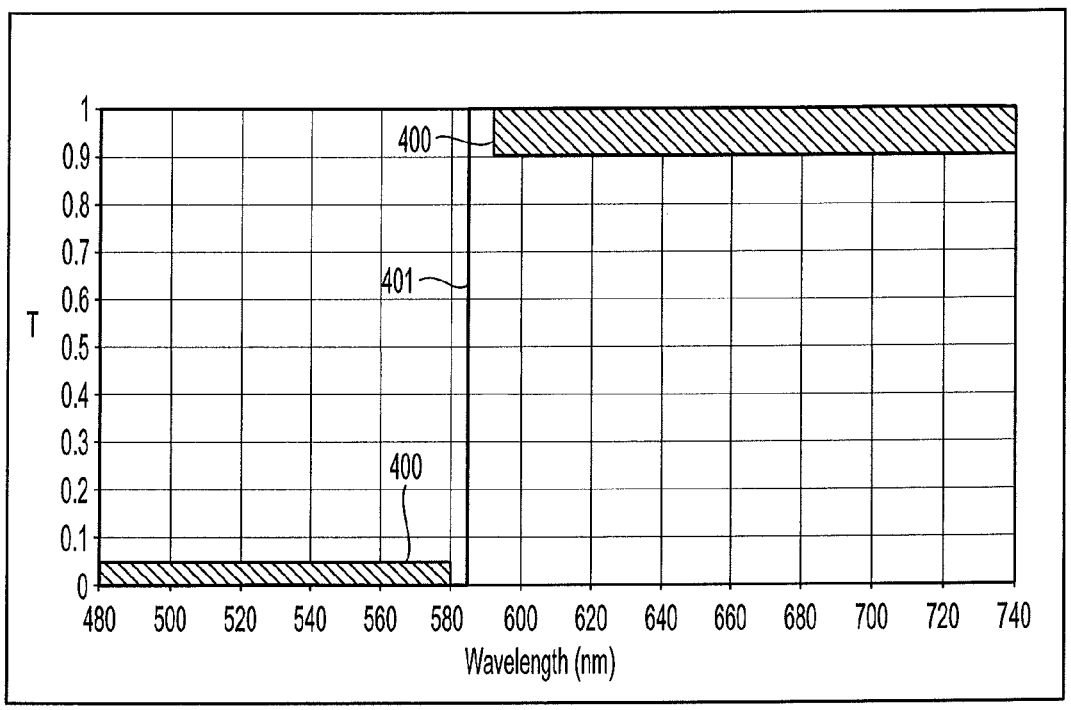
FIG. 4 depicts an exemplary product optical specification and an exemplary optical filter meeting the specification (target function) according to one aspect of the present disclosure.

For example, a long-pass optical filter that reflects light from 480 nm to 580 nm at level higher that 95% and transmits light from 590 nm to 740 nm at level higher that 90%. The specification is shown in FIG. 4 as two shadowed areas of the spectrum 400.

2. After the process starts 301, the first step is to prepare the control system 302 and the associated monitoring software.

This step involves initialization of the system, taking reference measurements, issuing warning signals in case of malfunction, opening new process windows, creating initial files, specifying monitoring ranges, specifying sampling frequencies, etc.

3. Based on the needed product specification, a target spectral performance [T(λ)] 303 as shown in FIG. 4 as a constant dark line 401 can be set up.

In many cases the target spectral performance 401 can exceed the product specification 400 due to manufacturing reasons such as ensuring higher manufacturing yield, accounting for optical loss due to material scattering, specimen absorption, etc. Taking into account the product specification 400, the target spectral performance 401 can be an optical filter that reflects all the light from 480 nm to 585 nm and transmits all the light from 585 nm to 740 nm.

4. Input the initial parameters of the coating design 304, such as refractive indices and extinction coefficients of the surrounding medium, specimen and the materials to be used in the coating, angle of incidence, material dispersion, thickness of the specimen, tolerances, etc.

5. Define a figure of merit (merit function) MF 305

MF is designed to measure the agreement between the target [T(λ)] and the product design [M(λ)] and is usually small when the agreement is good. A number of figures of merit can be defined, such as least square fit, power function, exponential fit, etc. One example of a figure of merit is the Root Mean Squared RMSE:

$$MF = \sqrt{\frac{\sum_i \{[[T_i(\lambda)] - [M_i(\lambda)]]^2 \cdot \text{weight}_i^2\}}{\sum_i \text{weight}_i^2}}$$

where i refers to each particular wavelength specified in the target.

6. Setting up the boundary conditions 306: maximum number of layers, maximum thickness of the coating, minimum and maximum thickness of each individual layer, etc.

7. Generate initial coating design 307

Initial design is generated based on the input parameters and the characteristic matrix of the thin film-specimen system. In one exemplary non-limiting example, it is done by the following calculation:

$$\begin{bmatrix} B \\ C \end{bmatrix} = \left\{ \prod_{j=1}^{q} \begin{bmatrix} \cos\delta_j & (i\sin\delta_j)/\eta_j \\ i\eta_j\sin\delta_j & \cos\delta_j \end{bmatrix} \right\} \begin{bmatrix} 1 \\ \eta_s \end{bmatrix},$$

where $\eta$ is the layer optical admittance, defined as:

$\eta_j = N_j \cos\theta_j$ - for $s$-polarization $\eta_j = N_j/\cos\theta_j$ - for $p$-polarization where N is the complex refractive index, $N = n - ik$
where n is the refractive index of the film, $\kappa$ is it's extinction coefficient, d is it's physical thickness and $\delta$ is the optical phase $$\delta_j = \frac{2\pi \cdot (n_j - i\kappa_j)d_j}{\lambda_0} \cos\theta_j,$$

where $\theta$ is the angle of incidence and $\lambda_0$ is the wavelength
The product of the matrices is a 2×1 complex matrix $$\begin{bmatrix} B \\ C \end{bmatrix} = \begin{bmatrix} \alpha + i\beta\eta_s \\ \delta\eta_s + i\gamma \end{bmatrix}$$

The reflectance R of the system is given as:

$$R = \left(\frac{\eta_0 B - C}{\eta_0 B + C}\right)\left(\frac{\eta_0 B - C}{\eta_0 B + C}\right)^*$$

The transmittance is calculated as:

$$T = \frac{4\eta_0 \mathrm{Re}(\eta_s)}{(\eta_0 B + C)(\eta_0 B + C)^*}$$

The absorptance is calculated as:

$$A = 1 - R - T = (1 - R)\left(1 - \frac{\mathrm{Re}(\eta_s)}{\mathrm{Re}(BC^*)}\right),$$

where Re denotes the real parts of the corresponding complex number.
This calculation method is well known in the art and is not a subject of the current innovation. Other methods can also be equally applicable.

The matrix calculation starts from the bare specimen with optical admittance $\eta_s$ and proceeds forward towards the incident medium by adding layers with the boundary conditions met. The final result is a 2×1 matrix-column containing two complex numbers from which the reflectance, transmittance and absorptance are calculated. In some instances the initial design can be generated automatically by deploying different generation techniques such as needle synthesis, pattern searches or others. Yet, in another instances the initial design can be taken from a database.

One example of initial design that meets the above specification is: Glass//48.47H 41.84L 83.4H 53.35L 86.96H 37.66L 99.8H 36.61L 99.08H 53.35L 70.57H 74.27L 73.42H 61.72L 79.12H 59.63L 84.83H 53.35L 88.39H 53.35L 83.4H 56.49L 83.4H 60.68L 76.99H 64.86L 79.12H 61.72L 79.12H 57.54L 85.54H 52.31L 91.24H 47.08L 93.38H 50.21L 84.11H 60.68L 78.41H 66.95L 74.13H 66.95L 72H 69.04L 74.13L 64.86L 75.56H 27.2L 154.68H 26.15L 86.96H 57.54L 67.72H 84.74L 59.16H 76.37L 57.74H 85.78L 71.28H 85.78L 22.1H//Air, which comprises 61 layers of $Ta_2O_5$ (denoted as H) and $SiO_2$ (denoted as L), deposited of glass substrate. The numbers express the physical thickness of the layers in nanometers. One skilled in the art would understand the foregoing nomenclature.

8. Designate process control wavelength $\lambda_0$ 308

The process control wavelength $\lambda_0$ is chosen taking into account many practical considerations and is usually a matter of experience. For example, in case of monitoring in transmittance $\lambda_0$ can be chosen in wavelength range where the filter has high transmittance at all times during the deposition. The equipment limitations also have to be taken into consideration. In many cases the process of selecting monitoring $\lambda_0$ involves additional simulation. In our specific example we have chosen $\lambda_0 = 610$ nm. Once $\lambda_0$ is chosen the thickness of all layers can be expresses in quarter-wave optical thickness at $\lambda_0$, or m, using the conversion $$m = \frac{4nd}{\lambda_0}.$$

In some cases, more than one fixed control wavelength can be designated and monitored. It could be beneficial for certain applications such as optical comb filters, some multi-notch filters and others. In some cases it is also beneficial to switch from one control wavelength to another during the process of operation. These options are also included in the disclosed algorithm and in the operation of the optical control system under this disclosure.

9. Designating spectral range of scanning $\Delta\lambda$ 309

In some practical cases the monitoring of the deposited coating can be done in spectral domain by scanning a certain spectral region $\Delta\lambda$. For example the spectral range can encompass $\lambda_0$, $\Delta\lambda_1$-$\lambda_0$+$\Delta\lambda_2$. In other cases $\Delta\lambda$ can be a spectral range that does not include $\lambda_0$. It can be done as independent monitoring or in combination with the monitoring in time domain at $\lambda_0$. The monitoring may cover a region that is shifted towards the shorter wavelengths in relation to $\lambda_0$. One reason for this could be the fact that the spectral performance at the smaller wavelengths is richer in details and easier to use as reference. Another reason can be that, as the optical thickness increases during the process, the spectral peaks drift towards the longer wavelengths. For example, if a peak is expected at $\lambda_0$ during deposition, one could monitor how this peak gradually drifts from $\Delta\lambda_1$-$\lambda_0$ to $\lambda_0$ and predict the exact time when the peak will reach $\lambda_0$. This important feature can be used as additional means (combined with the monitoring at $\lambda_0$) to predict the moment when the right optical thickness of the individual layers is reached. Yet, a third reason to extend the spectral monitoring towards lower wavelength range is in those cases when the diffuse component of the measured light is important, since optical scattering affects the lower wavelength range stronger.

As an example, the monitoring wavelength $\lambda_0$ for a typical amorphous silicon solar cell can be chosen in the spectral area of low absorption of the material (Urbach tail), such as 850 nm. This choice provides opportunity to monitor in real time the material bandgap by monitoring "constant absorption level". The spectral range $\Delta\lambda$, can be chosen in the visible range, for example, 300 nm to 1000 nm. This choice allows, first, monitoring the optical scattering of the material under deposition and, second, as the growing film becomes opaque in the visible range, the interference peaks in the near infrared region, where the material is transparent, can be used.

In other cases, the spectral domain monitoring can be performed entirely independent of the monitoring at $\lambda_0$ or/and at different angles of incidence than the monitoring at $\lambda_0$. This can be beneficial for monitoring the behavior of solar cells, special polarization filters, dichroic filters, filters designed to operate at large angle of incidence, filters operating and more than one spectral band, filters deposited on aspheric surfaces or thin film micro-lenses, photonic crystals and others.

In still other cases, more than one spectral range can be chosen for spectral domain monitoring, or one range $\Delta\lambda$, can be replaced with another during manufacturing. This is also included as an option in the disclosed algorithm and control system. As in the case of the time domain monitoring, the process of spectral range designation $\Delta\lambda$, should not be considered limited and restrictive.

10. Optimizing the design 310

The design optimization involves minimization of the [MF] by deploying different optimization methods such as Simplex, Monte-Carlo, Levenberg-Marquardt, Hooke & Jeeves, etc. The search for minimal value of the figure of merit [MF] involves many iterations and usually requires deployment of more than one optimization method. Usually the optimization process starts with choosing a global optimization method such as Global Simplex and later changing it to a local optimization method.

For example, the optimization can lead to the following coating design, which comprises 61 layers of $Ta_2O_5$ (denoted as H) and $SiO_2$ (denoted as L). The numbers express the optical thickness of the layers in relative units of quarter-wave optical thickness at $\lambda_0$=610 nm, or the number m, assumed to be the coating monitoring wavelength in transmission. For example 0.674H denotes optical thickness of the H layer (n=2.14 at 610 nm) d=0.674 (610 nm/(4n))=48.03 nm. In this example the refractive index of the L material at 610 nm is 1.467.

Glass//0.68H 0.4L 1.17H 0.51L 1.22H 0.36L 1.4H 0.35L 1.39H 0.51L 0.99H 0.71L 1.03H 0.59L 1.11H 0.57L 1.19H 0.51L 1.24H 0.51L 1.17H 0.54L 1.17H 0.58L 1.08H 0.62L 1.11H 0.59L 1.11H 0.55L 1.2H 0.5L 1.28H 0.45L 1.31H 0.48L 1.18H 0.58L 1.1H 0.64L 1.04H 0.64L 1.01H 0.66L 1.04H 0.62L 1.06H 0.26L 2.17H 0.25L 1.22H 0.55L 0.95H 0.81L 0.83H 0.73L 0.81H 0.82L 1H 0.82L 0.31H//Air.

Figure 5:
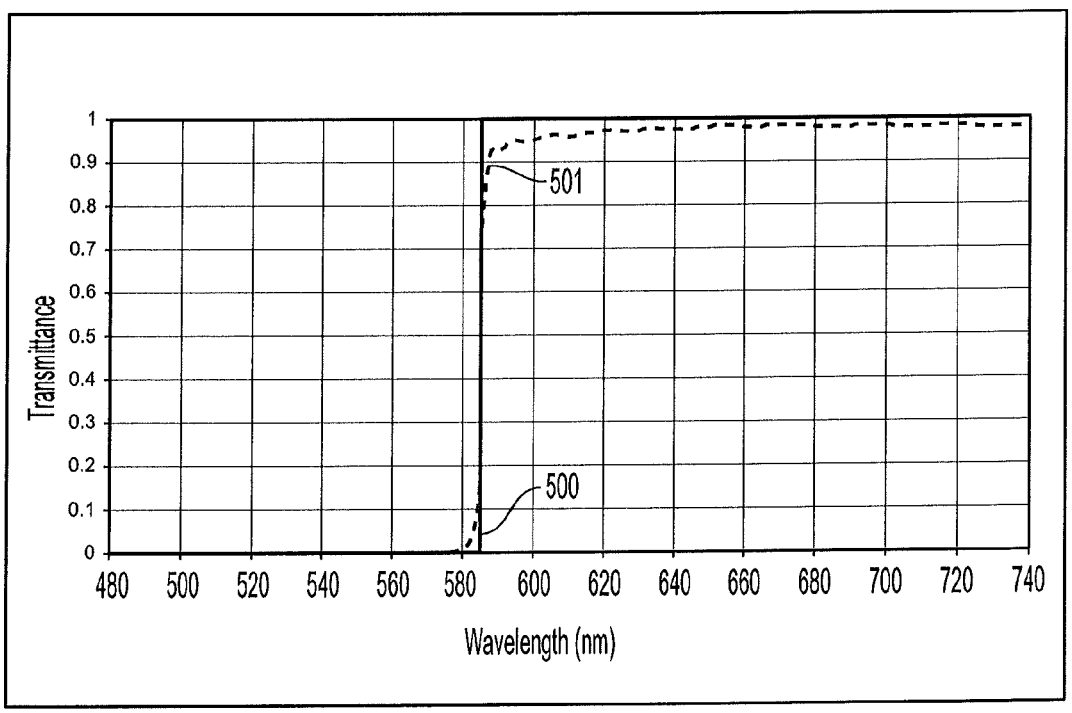
FIG. 5 depicts the exemplary target function in comparison to an example of a designed optical filter meeting the target specification, according to one aspect of the present disclosure.

With reference to FIG. 5, the dashed curve 501 compares the spectral performance of the designed coating as opposed to the ideal (target) coating 500.

11. Set the measurement tolerances 311.

The measurement tolerances can be set tight in case of very precise, stable, vibration-free and other highly controlled environment, or can be relatively loose to avoid random errors in case of a not very well controlled environment. The properties of the light sources, light detectors and other system components may also determine how tight the tolerances can be chosen.

12. Generate theoretical target optical monitoring function at $\lambda_0$ 312

Figure 6:
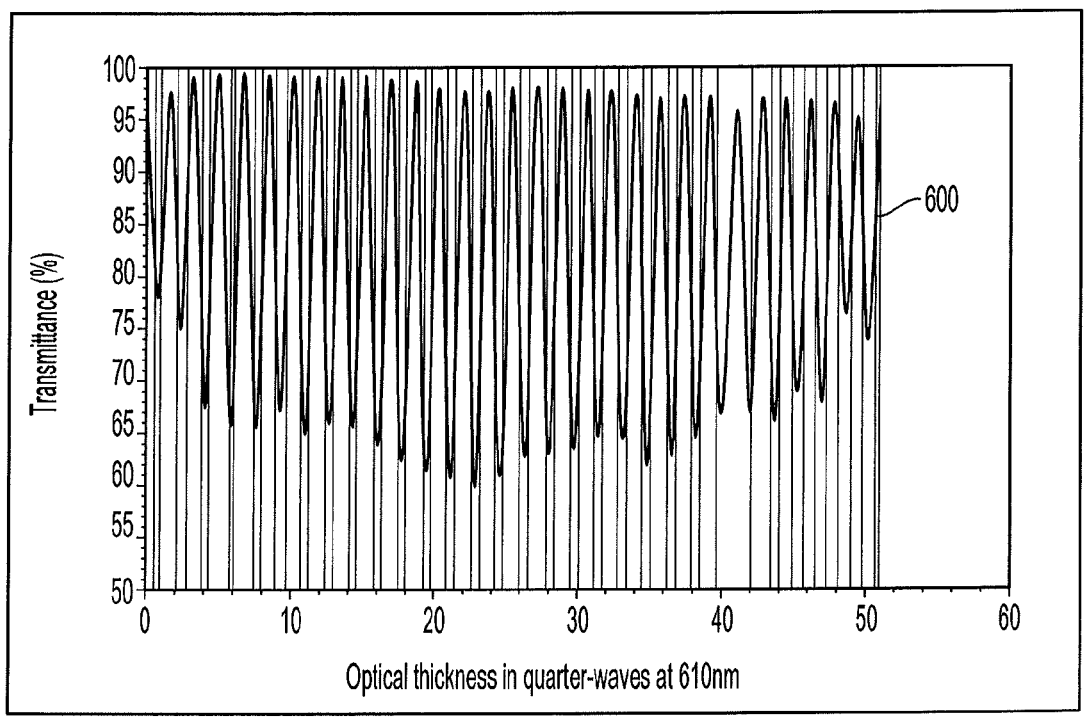
FIG. 6 depicts a monitoring function (for optical transmission) as a function of optical thickness in units of quarter-wave thickness at 610 nm (time domain), according to one aspect of the present disclosure.

The theoretical target optical monitoring function can be generated based on the optimized design. It can be done by reverse calculation, when each of the 61 layers is split into many small fractions and the transmittance after each fraction is calculated. For example, in this calculation, each of the 61 layers is split on 150 sub-layers. However, this number can be significantly larger or smaller depending on the complexity of the filter. Each sub-layer may represent an intermediate target value which is supposed to be reached during the process (intermediate target). FIG. 6 illustrates the monitoring curve 600 which shows the evolution of the filter in terms of change in transmittance of the system specimen-coating as the coating is deposited (time domain). Starting from T of the bare specimen, T changes depending on the optical thickness of the deposited layers until the final spectral performance is reached. It can be seen that the monitoring function changes periodically with a period related to the quarter-wave optical thickness of the deposited coating.

13. Generating series of intermediate targets within $\Delta\lambda$ 313

Using the optimized coating design, targeted spectral performances (intermediate targets within $\Delta\lambda$) can be generated frequently during the deposition process and compared with the real spectral performances of the deposited thin films. In many cases scans are made within $\Delta\lambda_1$-$\lambda_0$+$\Delta\lambda_2$ and each theoretical spectral performance is used as an intermediate target, which has to be achieved during the real deposition process. In some other cases, the spectral scans are independent of the measurement at $\lambda_0$ and used as a second reference source. The intermediate targets can be generated and the spectral measurements can be done constantly or with a certain chosen frequency, not necessarily the same as those in the time domain.

Figure 7:
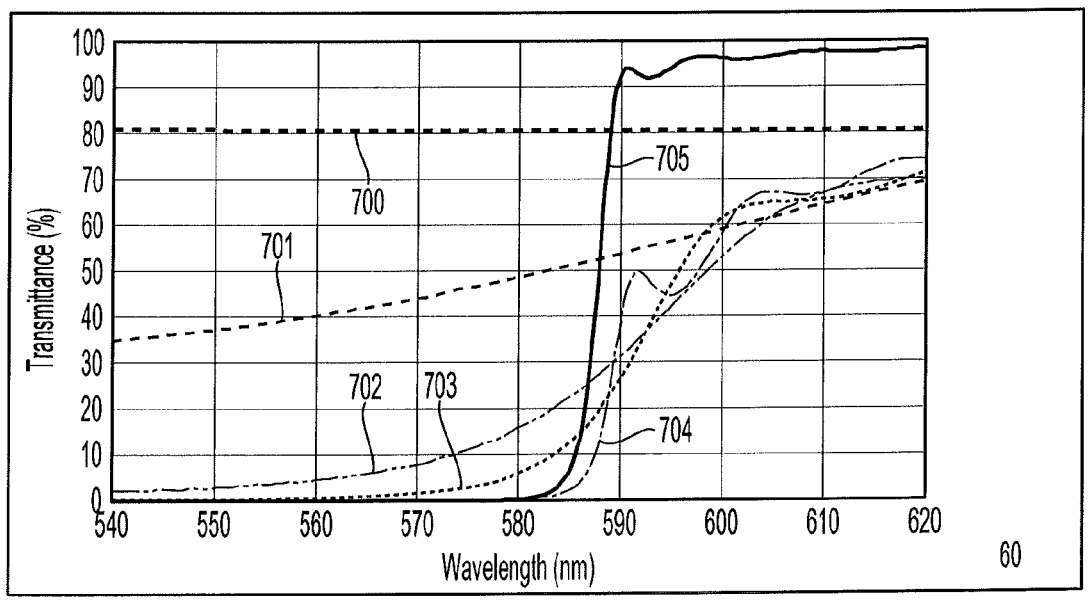
FIG. 7 shows a graphic representation of exemplary target spectral performances (intermediate targets) of the filter from 540 nm to 620 nm (spectral domain) after layer 1, 2, 7, 17, 25, 51, and 61 (complete filter) according to one aspect of the present disclosure.

FIG. 7 shows several theoretical spectral performances (intermediate targets) of the filter in our chosen range of scanning $\Delta\lambda_1$-$\lambda_0$+$\Delta\lambda_2$, where $\Delta\lambda_1$ is chosen as 70 nm and $\Delta\lambda_2$ as 10 nm, or from 540 nm to 620 nm after layer 1 (curve) 700, 7 (curve) 701, 17 (curve) 702, 25 (curve) 703, 51 (curve) 704 and 61 (last layer) 705 are deposited (4=610 nm).

14. Generate process recipe 314.

The process recipe can be pre-recorded and retrieved from the database, generated as a standard form of operations and process conditions, which is filled by the equipment operation engineer, created manually or in some other way.

15. Starting the deposition process with layer #1 315.

16. Scanning and measuring in real time optical performance 316 as the film is deposited.

17. Creating a moving average from data stream at $\lambda_0$ 317.

The software can be designed to form a moving average value (boxcar value) comprising many measured data points. Each time a measurement is made, the moving average changes by adding a new data point in front of the numerical sequence and dropping the last data point of the sequence. For example, if the measurements are performed (or measured signal is sampled) with frequency of 1 KHz, a moving average can be created, which may have 100 data points when the monitoring curve is far from an extremum, but changes to a smaller number of data points (for example 5 data points) when a sharp extremum is approached. The amount of data points in the sequence is calculated by the software in real time, depending on the behavior of the monitoring function. Since different extrema have different sharpness (usually in transmission maximums are sharper than minimums) for the different materials deposited (materials with higher refractive indices have sharper extrema), the software adjusts the number of the numerical sequence in real time by taking into account the behavior of the theoretical monitoring function. This feature can be designed in such a way as to avoid random errors generated during the monitoring process.

18. Plotting in real time the measured monitoring function 318 over the intermediate target functions at $\lambda_0$.

A computer screen is open where the calculated and measured curves are plotted in real time.

19. Comparing the two curves in real time 319. Make real time decision 320 about the observed behavior of the measured curve.

If a deviation is recorded 320, the system makes a decision regarding the magnitude of the deviation. If it is larger than the set tolerance, the system stands on alert 321 in order to determine if the deviation is systematic or random 322. Systematic deviation means that the deviation is either growing steadily during several monitoring cycles or is constant and not changing with time. Certain small deviations from the calculated target can be due to some small random changes in the process parameters such as temperature change or pressure drift, which are usually corrected by the equipment feedback control. In such cases the monitoring system may disregard the change. However, if the deviation increases steadily during the deposition, this might be a sign that some of the optical constants of the deposited films are changing.

20. Calculating ahead of time the effect on the figure of merit [MF] 323 and on the product specification.

This step is designed to verify if the observed deviation leads to a product not meeting the product specification. In this calculation, the program may assume that the deviation in the property of the current layer has already taken place and will continue to be present until the end of the layer, but all other layers which are waiting to be deposited, will be the same as the initial design.

If the product specification is met, the process continues at position 338.

21. If the product specification is not going to be met 324, from the measured deviation, the program calculates the new layer parameters 325 such as new optical constants, new layer thicknesses, and generates new product design where only the layers remaining to be deposited, are corrected. This operation may be performed seamlessly.

22. The program optimizes the new design with the new parameters 326 to minimize the merit function [MF] and generates corrected product design, new target monitoring function at $\lambda_0$ 327, intermittent spectral targets 328 and, if necessary, a new process recipe 329.

Figure 8:
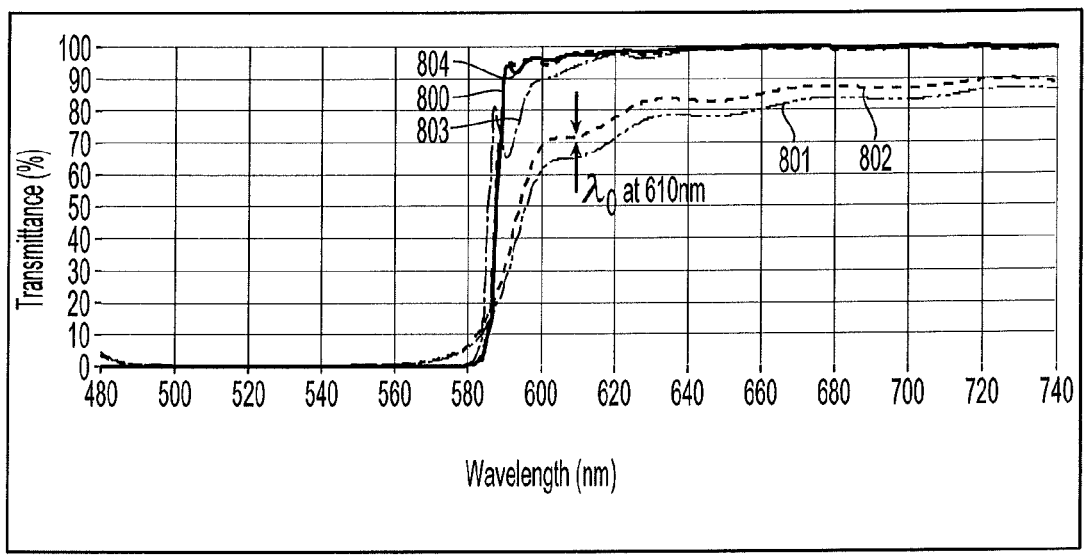
FIG. 8 shows optical transmittance as a function of wavelength for a 61-layer filter showing effects of correcting an error at layer 25.

FIG. 8 shows a static "snapshot" picture of the effects of the software algorithm in the example of the 61-layer cut-off filter. It presents the optical transmittance as a function of wavelength (spectral domain), both with and without error correction at layer 25. Curve 800 shows the initial design of the 61-layer cut-off filter with the initial parameter input. Curve 801 shows how the filter looks after layer 25, assuming that all 25 layers are deposited correctly (intermediate target). However, if layer 25 finishes with an error 802, the spectral performance of the filter after layer 25 drifts from its pre-designed one. The error, which is introduced in this case, is very small: only 7 nm under-deposition of layer 25 changes the transmittance value at 610 nm with about 7%. Such an error can be due to change in the refractive index of the deposited material or can be due to some error in defining the end-time (cutting point) of the layer. Whatever the reason, if the process continues without addressing the error at layer 25, we will end up with a filter which does not meet the initial specification and will be a reject-curve 803. However, after correction in the remaining 36 layers to compensate for the error in layer 25, we end up with curve 804 which again meets the product specification.

Figure 9:
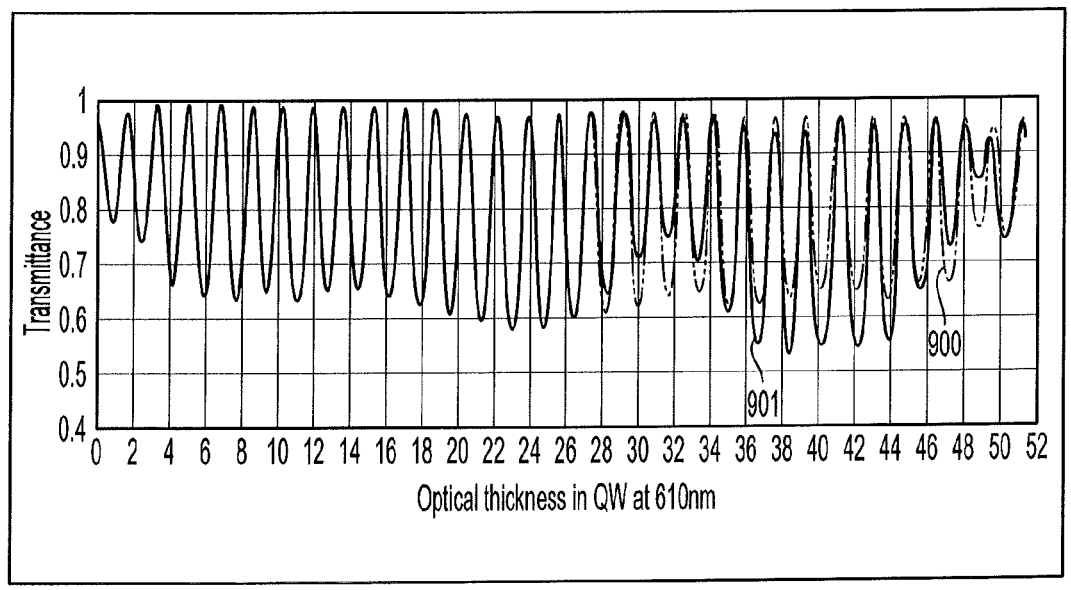
FIG. 9 illustrates the change in the monitoring curves if a systematic variance builds up around layer 25, which, if not corrected, results in the filter not meeting the product specification, according to one aspect of the present disclosure.

FIG. 9 illustrates how the monitoring curve in time domain at $\lambda_0$=610 nm will change if the error is not corrected (curve 901) in comparison with the filter without any error in layer 25 (curve 900). The two curves start deviating one from another not immediately, but some time after the erroneous layer 25. In reality, if the error is discovered 4-5 layers after it were made, there are very limited opportunities for it to be corrected. The main reason is not only that there are a fewer number of layers remaining to be re-optimized, but because it is extremely difficult to pinpoint the error back in time. For example if the deviation was discovered at layer 31, it is practically not possible to pinpoint the error at layer 25. It could easily be at layer 24, or 26, 27, or elsewhere. Therefore, it is best to be able to locate the error as soon as possible after it is made. One advantage of the present invention is the fact that the optical control system pinpoints the errors very soon after they are happening. This can be achieved by monitoring the thin film process locally, in close proximity to the deposited surface, by positioning the optical sensors inside the deposition chamber. One example for new design formula after re-optimization is as follows:
Glass//0.68H 0.4L 1.17H 0.51L 1.22H 0.36L 1.4H 0.35L 1.39H 0.51L 0.99H 0.71L 1.03H 0.59L 1.11H 0.57L 1.19H 0.51L 1.24H 0.51L 1.17H 0.54L 1.17H 0.58L 0.98H* 0.68L 1.12H 0.74L 0.97H 0.5L 1.19H 0.57L 1.35H 0.45L 1.25H 0.44L 1.17H 0.6L 1.16H 0.65L 1.02H 0.59L 1.01H 0.67L 1.09H 0.62L 1.02H 0.26L 2.14H 0.25L 1.22H 0.57L 0.99H 0.76L 0.83H 0.7L 0.86H 0.8L 1.01H 0.8 L 0.31H//Air, where the flawed layer 25 is denoted with *.

The difference between the original and the corrected designs is very small and in fact might not be detected by the analytical tools, if the filter is examined after the deposition.

In some embodiments, the control system of the present disclosure pinpoints the error within a very short time interval after it occurs. It takes a small number of iterations (typically lasting few tens of seconds) to perform all validation procedures and confirm that an error has been made and that the final product specification or the set target is not going to be met, unless the error is not corrected. After this is confirmed, calculations are made to determine what causes the change. It could be a refractive index, absorption, contamination, bandgap drift, etc. In order to determine the cause, the system may predict a change in one parameter in time domain and validate it in the spectral domain. Specifically, in the case of change in optical constant (refractive index, absorption, scattering, etc) it is very convenient to go iteratively back and forth between the two domains until a good agreement is achieved. This process is known in the art as iterative prediction (also iterative mapping). Once this is done, the control system inputs the new thickness of the erroneous layer #25 into the design formula and re-optimizes layers 26-61 in order to compensate the error and return to the desired specification, i.e., achieve acceptable figure of merit. Therefore, the described method performs the corrective process seamlessly and can be done without human involvement.

In the example of deposition of amorphous silicon solar cells in a superstrate process, the system may detect that the light scattering of the TCO layer during deposition is smaller than the targeted value. This may require on-the-run increasing the end thickness of the TCO layer in order to compensate for the reduced light trapping and achieve the same light trapping in the absorber needed to meet the specified conversion efficiency of the solar cell. Alternatively, the software may increase the thickness of the amorphous silicon absorber layer in order to achieve the same effect. At position 325, the software program calculates a new product design to reflect the real conditions on the surface of the specimen and re-optimizes it 326 for best results.

23. Steps (or "positions") 330 thru 337 in FIG. 3 are performed in parallel with steps 317 thru 324. As the film is being deposited, the system records the measured spectral scans 330, displays them over the calculated spectral curves 331 and compares the two curves 332. This is done multiple times and not necessarily with the same periodicity as the measurements at $\lambda_0$.

24. Next is a decision point 333 where the system decides whether the deviation between the two curves is larger than the tolerance. If it is not larger, the system continues monitoring the process—position 338. If the deviation is larger the system records the event and stays in an alert position 334 to determine whether the deviation is a random error or there is a constant deviation building up—decision point 335. If the deviation is due to some random fluctuation and is not systematic, the system continues the monitoring process 338. If the deviation is judged as systematic, the system calculates the effect of the deviation on the merit function [MF] 336 and decides whether the product specification will be met with the measured systematic deviation 337. If the product specification is still met within the specified tolerance, no further action is needed and the system continues the process at step 338. If the specification is not going to be met, the system performs the already described action items 325 to 329.

There are several reasons why the system could be configured to perform parallel monitoring in the time domain and in the spectral domain.

One reason is that in practice, the measurement in time domain is much more accurate due to the availability of stable laser sources with sufficient optical power and availability of stable low chirp optical modulators. However, monitoring only in the time domain very often does not provide sufficient information to perform all the calculations with sufficient certainty. There are too many factors, which can affect negatively the time domain monitoring as well. Some factors are not related to the monitored film at all, such as misalignments, sensitivity to temperature gradients inside the chamber, among others. On the other hand, monitoring only in the spectral domain only has its own drawbacks as well. The available broadband light sources do not have sufficient total power, which, in addition, is very often wavelength dependent. For example, white light LED sources typically operate in the range of 420 to 720 nm with significant wavelength dependence. The typical incandescent light sources provide good wavelength independency and extend deep into the near infrared region, but provide insufficient light power per wavelength and have many other engineering disadvantages (low lifetime, heat generation, long stabilization times, difficulty to modulate directly, etc.)

A second reason is that typically the spectral domain measurements require longer time than the time domain measurements. While in the time domain a single optical power meter or light detector can be used, in the spectral domain there is a need for spectrally dispersive components such as a spectrometer or an optical spectrum analyzer, which typically have larger acquisition times.

To take this into account, one can use the time domain measurements as main process data for the calculation of the needed parameters, while the validation and accuracy of the calculations can be done in the spectral domain. This priority, however, is not restrictive and people skilled in the art may use the two domains interchangeably, or use only one of the two domains.

For further clarity, consider the example where, based on the time domain measurements, the system determines that the index of refraction of the deposited film may be dropping by 3%. However, such a signal change can be due to variety of other reasons, unrelated to the refractive index. Slight temperature change inside the deposition equipment may lead to some small misalignment of the monitoring device or contamination of the sensor may take place, or other reasons. Therefore, the prediction that the refractive index changed needs validation. At the same time, if the refractive index changes at $\lambda_0$, it changes over the entire spectrum $\Delta\lambda$. The monitored spectral extrema will display proportional drift as well. Their drift can be determined and used to validate the prediction that the refractive index has changed. In the same note, if from the time domain measurements the system determines that the absorption coefficient has changed, the prediction can be validated in the spectral domain by measuring the absolute values of the extrema and by monitoring the form and the slope of the envelope curves.

25. At decision point 339, the system decides whether the current layer is already completed or not. If the layer is not completed the system will repeat the procedures starting from position 316 until the layer is deposited, after which it will send a signal to start another/next layer 340.
26. At position 341, the system again verifies whether the final product specification is met and it is the case the entire process ends 341. If the product specification is still not met it would obviously have more layers to deposit and the system returns to position 316.

A person skilled in the art would appreciate that the algorithm described above can be applied with some modifications to meet various requirements. Modifications are made in the cases of thin film solar cells, thin film etching and deposition through shadow or contact masks or laser ablation. Thus, any foreseeable modifications and applications are within the scope of the present disclosure.

The deposition of the thin film solar cells can be monitored in transmission or reflection or both at various incidence angles and/or other conditions. Transmission is preferred when the optical thin film structure is manufactured on a transparent specimen and the thin films are also transparent "superstrate process". Monitoring in transmission facilitates the alignment of the optical system compared to monitoring in reflectance. However, most solar cell thin films can be monitored using in-situ monitoring in reflection. In some cases, the preferred reflectance monitoring is done from the back side of the substrate (uncoated side). This configuration has several advantages and is the preferred solution for monitoring solar cell deposition in a superstrate process. One of the advantages is that the monitored sensors are protected from the deposition material and remain not obstructed by any machine parts or material. Also, reflectance monitoring from the back side of the specimen is a very good option when deposition is made through shadow or contact mask, as is the case with some thin film micro-lenses and other patterned thin films. In other cases, monitoring the specular transmittance or reflectance is not enough and the diffuse (scattered) parts of the transmittance or reflectance have to be measured as well. This is the case when solar cells, nanostructures, photonic crystals or some other two-dimensional structures are manufactured. Yet, in another cases (such as manufacturing of nanostructures) the monitoring can be performed at very close proximity to the surface of the specimen in order to capture the near-field light scattering and, through it, the characteristics of the structure under formation.

Figure 10A:
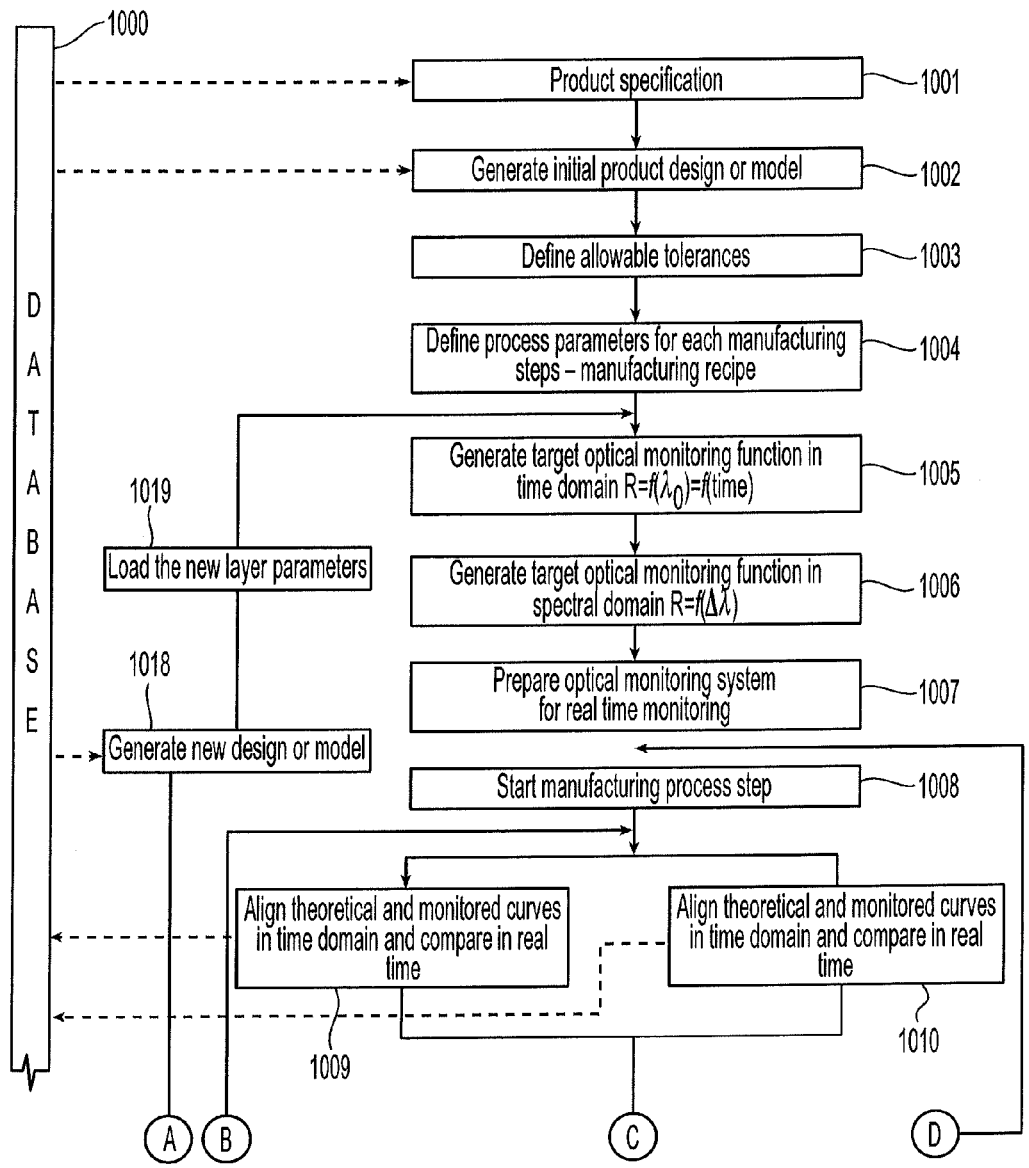
FIG. 10 shows a flow chart of a method of control of surface modification process for forming a thin film solar cell in which the monitoring of the spectral reflectance is used in order to determine the optical constants and other important parameters of the deposited film and adaptively change the product design according to one aspect of the disclosure.
Figure 10B:
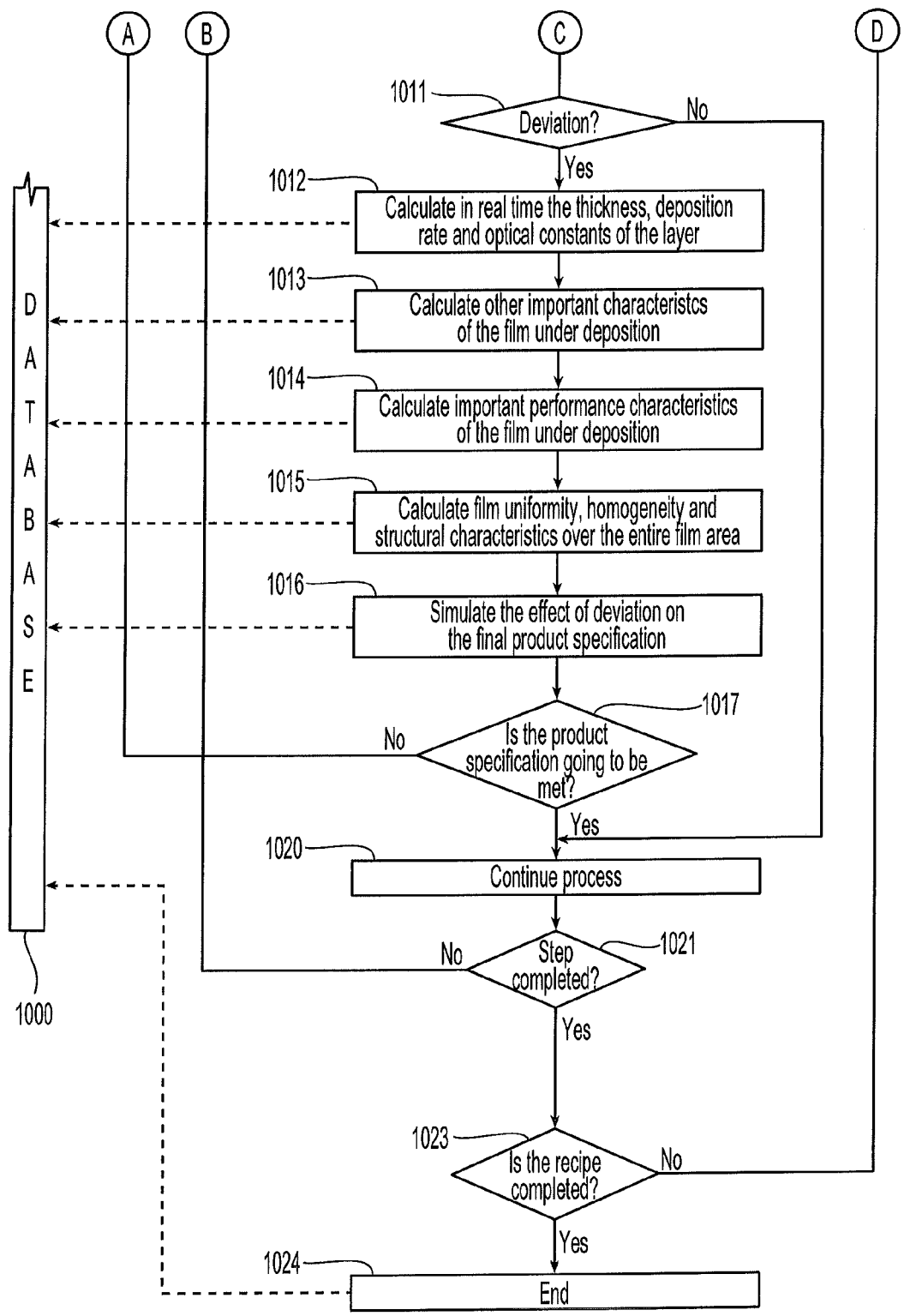

FIG. 10 shows one specific non limiting example of a flow chart of a method for control of surface modification process for forming thin film solar cell according to one aspect of the disclosure. The monitoring of spectral transmittance or reflectance is used in order to determine the optical constants of the deposited thin films in real time. The usual calculation algorithm follows the classic Valeev turning point method, as explained in A. S. Valeev, *Optics and Spectroscopy*, Vol. 15 (1963) 500-511 and developed further by Swanepoel, R. Swanepoel, J. *Phys. E: Sci. Instrum*, Vol, 16, (1983) 1214-1222, familiar to those skilled in the art.

The determination method of the film parameters is based on the evaluation of the envelope curves connecting the reflectance minima and maxima at one fixed wavelength. One way to perform the calculation is by following some known approximation to express the optical transfer function of the thin film, such as:

$$\begin{bmatrix} B' \\ C' \end{bmatrix} = \begin{bmatrix} \left(\frac{N_{in}}{N_{out}}\right)^{1/2} \cos\delta & \frac{i}{(N_{in}N_{out})^{1/2}} \sin\delta \\ i(N_{in}N_{out})^{1/2} \sin\delta & \left(\frac{N_{out}}{N_{in}}\right)^{1/2} \cos\delta \end{bmatrix} \cdot \begin{bmatrix} B \\ C \end{bmatrix}$$

where $N_{in}$ and $N_{out}$ are the complex refractive index values of the specimen near the film-specimen interface and near the measured surface respectively, $$\delta = (2\pi/\lambda) \int_0^d [n(z) - ik(z)] dz$$

is the phase for normal incidence, n and k are the real part and the imaginary parts of the complex refractive index, d is the layer thickness and z is the distance from the interface film-specimen, or the attained thickness of the film at that one specific moment. The characteristic matrix $$\begin{bmatrix} B \\ C \end{bmatrix}$$

represents the monitored specimen before the beginning of the deposition process and has to be known.

As the film starts growing on the specimen the complex matrix product $$\begin{bmatrix} B' \\ C' \end{bmatrix} = \begin{bmatrix} \alpha + i\beta \\ i\gamma + \delta \end{bmatrix}$$

changes in real time. The resultant reflectance is given as $$R = \frac{(B'-C')(B'-C')^*}{(B'+C')(B'+C')^*}$$

(for measurement performed in air/vacuum). The task is to measure the reflectance of the film in real time, determine the envelope related to the minima and maxima $R_{min}$ and $R_{max}$ of the reflectance curve and calculate the optical constants n(z) and k(z) at the attained thickness of the film at that moment. Once the optical constants n(z) and k(z) are determined at $\lambda_0$ they can be validated by the spectral curves in the spectral domain and reconstruction of the spectral dispersions of the newly derived constants n($\lambda$,z) and k ($\lambda$,z) can take place.

The optical absorption coefficient $$\alpha(\lambda, z) = \frac{4 \cdot \pi \cdot k(\lambda, z)}{\lambda}$$

can be calculated and used to calculate the film material bandgap by using some adopted in the art linear extrapolations such as Cody's extrapolation:

$$\sqrt{\alpha \cdot n/E} = B(E - E_g),$$

where E is the photon energy, $E_g$ is the energy of the material bandgap and B is a constant. In this way the film material bandgap is calculated as the film is being deposited and displayed as a function of the attained thickness of the film at that moment $E_g(z)$.

In many cases of deposition of photovoltaic solar cells, it is important to measure the surface roughness of the film. The surface roughness is an important parameter related to the film morphology and is responsible for the light trapping inside the absorber. It has been shown that increasing the surface roughness can reduce significantly the thickness of the absorber films for the same value of light absorptance, as discussed in Lundberg et al., Progr. Photovolt.: Res. Appl: 11, 2003, p. 77-88.

A control system, based on miniature fiber optic sensors installed at specific points in existing film deposition equipment allows positioning of the sensor in very close proximity to the deposited surface and monitoring the specular and diffuse spectral reflectance R from the film as the substrate moves throughout the deposition chamber. The measurement of spectral scattering allows the calculation of the parameter haze: $H_R = R_{diffuse}/R_{total}$ and its angular distribution.

The scalar scattering theory relates the haze to the surface roughness $\delta_{rms}$ of the film by:

$$H_R = 1 - \mathrm{Exp}\left[\left(\frac{4 \cdot \pi \cdot \delta_{rms}}{\lambda}\right)^2\right].$$

The measuring of the diffuse component of the reflected light $R_{diffuse}$ is also important for the accurate calculation of the film material bandgap Eg. Typically, in the UV and in the visible spectral ranges, the optical loss measured by the sensors is due not only to the absorption of light, but also by light scattering. Therefore, $R_{diffuse}$ is needed for the accurate calculation of $\alpha(\lambda,z)$ in the UV and visible range, and, subsequently, for the accurate calculation of the material bandgap $E_g$. This is particularly an important problem for the calculation of $E_g$ of the amorphous silicon absorber films, which have relatively large bandgap and the Eg determination is more strongly affected by the light scattering.

Monitoring of light scattering is specifically important in the manufacturing of solar panels when the monitoring is performed from the back side of the substrate. This is because the monitoring beam is able to penetrate through the transparent substrate and through all the deposited films, and reflect from the interface where the film deposition takes place. The first film, deposited immediately on the substrate, is the transparent conductive oxide (TCO) film, which is designed to have strong scattering properties in order to trap more light into the silicon absorber. The scattering of the TCO, as well as its change in time, are important for the accuracy of monitoring of the overlaying amorphous silicon film. In addition monitoring sensors can be used to distinguish among the types of light scattering taking place in the monitored film.

Another application where monitoring of light scattering is important is the manufacturing of micro and nano-structured thin films and devices, where monitoring of near-field scattering from the surface where the structure is formed provides timely information about the nano-particle growth condition, the type, dispersion and geometry of the monitored structures. Monitoring light scattering is also important in many other surface modification processes such as surface polishing, printing and ion implantation.

The entire control process for solar cell manufacturing, as shown in FIG. 10, starts with the generation of an initial product design or model 1002 which meets the initial product specification 1001. The generation of the initial product design or model may be also a process of simple selection of an appropriate product design or product model from the system database 1000. Next the allowable tolerances 1003 are specified, such as allowable thickness change, uniformity, desired bandgap accuracy, scattering loss, surface roughness, etc. At step 1004 all process parameters are defined to form a specific manufacturing recipe. The recipe might also be retrieved from the database 1000.

Following is the generation of theoretical target optical monitoring functions, which, if followed, will ensure that the photovoltaic structure will meet the product specification 1001. Step 1005 shows the target monitoring function in time domain (the change in reflectance R at $\lambda_0$ as the films are being deposited in time) and step 1006 shows the target monitoring function in spectral domain (the change in reflectance R within a chosen wavelength range $\Delta\lambda$ as films are being deposited in time). As before, $\lambda_0$ do not have to be in the $\Delta\lambda$ range. Very often the wavelength range extends from ultraviolet to visible and near infrared region to encompass spectral ranges from the zone of high absorption of the absorber to low absorption (Urbach zone) to no absorption.

For example, in the case of monitoring amorphous silicon solar cells, the monitoring wavelength $\lambda_0$ can be chosen at 850 nm, where the silicon absorber thin film has very low (but still measurable) absorption, while the range $\Delta\lambda$ can be chosen to be 300-1000 nm. The monitoring at the lower range 300-600 nm is needed in order to measure the light scattering, while the range 500-1000 nm provides the spectral interference information needed for the calculation of $n(\lambda,z)$ and $k(\lambda,z)$. Similarly, in the case of monitoring CIGS $\lambda_0$ can be chosen at 1310 nm, where the CIGS absorber has low (but measurable) absorption, while the range $\Delta\lambda$ can be chosen to be 300-2000 nm.

In many cases in solar panel deposition, the substrate has already one or several deposited thin films on it. Many manufacturers start the deposition of the solar panel with already deposited transparent conductive oxide layer (TCO) or with already-deposited metal mirror. The necessary calculations to account for the already deposited films can be taken during steps 1005 and 1006.

It is understood that the above spectral are merely exemplary. Also, the chosen spectral range does not have to be covered by one single light source, sensor or light detector. A variety of light sources such as LEDs, incandescent lamps, tunable lasers, etc, can be used, and a variety of fiber optics assemblies, sensor configurations and light detectors such as spectrometers, optical power meters, photomultipliers may likewise be employed.

At step 1007, the monitoring system is prepared for the process of real time monitoring. This preparation may include system initialization, taking reference, sensor alignment, preparation of the hardware of data acquisition software or many other procedures.

At step 1008, the manufacturing process starts with the first manufacturing step.

As the film is deposited, the theoretically generated curves in time 1009 and spectral domains 1010 are plotted, aligned and displayed together with the curves built from the measured from the system real time data and constantly recorded. All real time information is recorded in the database 1000.

Together with the curves, the system calculates, displays and records the film thickness and deposition rate. In the case the theoretical and monitored curves match each other both in shape and in time, the film thickness and the deposition rate are the same as prescribed in the recipe. In case of offset of the curves in time, the calculation of the film thickness and deposition rate are adjusted by the system in order to match the measured curves with the theoretical ones. This operation is not marked on FIG. 10 to avoid confusion, but persons skilled in the art will understand that the calculation of these parameters is part of the operation of the monitoring system.

Next, in step 1011, the system decides whether there is a deviation between the curves that exceeds the tolerance accepted at step 1003. In case there is no such deviation, the process continues with step 1020. In case the deviation exceeds the tolerance, the system calculates 1012 new film thickness, deposition rate and optical constants $n(\lambda,z)$ and $k(\lambda,z)$ of the layer and records the deviation and the new parameter values in the database 1000.

At step 1013 additional film characteristics are calculated and recorded in the database such as the relative density of the film, film porosity, depth profiles of the parameters, non-homogeneity, etc.

Next, at step 1014, other important quality and performance characteristics of the film are calculated such as material bandgap, haze, surface roughness, micro-structural characteristics, etc.

At step 1015, the calculated characteristics from all sensors, monitoring the film in a parallel configuration, are compared and differential signals are calculated. Differential signal can be displayed between each two sensors and between each sensor and the target value. In this way entire surface mapping of the film can be created, containing the needed information for the film uniformity and parameter homogeneity over the area of the panel. All these calculations are also displayed on the screen and recorded in the database 1000.

After all calculations are made and all interested parameters are extracted, at step 1016, the system calculates the effect of the parameter change on the final product specification. This simulation may consist of searching the database 1000 for already recorded previous processes with the same or similar parameters, may consist of additional simulation or simple comparison with past products.

At step 1017, the system decides whether the final product specification will be met in order to continue the process in the same fashion 1020 or introduce changes. In the case when the system decides that the product specification is not going to be met, at step 1018 the system generates a new corrected product design or product model by either performing its own re-optimization or pulling it from the database.

At step 1019, the system loads the new calculated parameters from the new design or model and the process continues without any disruption.

At step 1021, the system determines whether the step is completed. If the entire step is completed, the system proceeds to step 1023 to see if the recipe is completed. If the recipe has not been completed, control passes back to step 1008 to carry out the next manufacturing process step. If, on the other hand, at step 1023 a determination is made that the recipe has been completed, the system records all the measured data, parameters, corrections and calculations in the database as a new product model and ends the process at step 1024.

By following the operation chart on FIG. 10, it can be ensured that the product specification will be achieved for most of the products. Also, most of the products will come out of manufacturing with a narrower distribution of properties. All this can be performed without human involvement by operating the monitoring system in the automatic mode.

Figure 11:
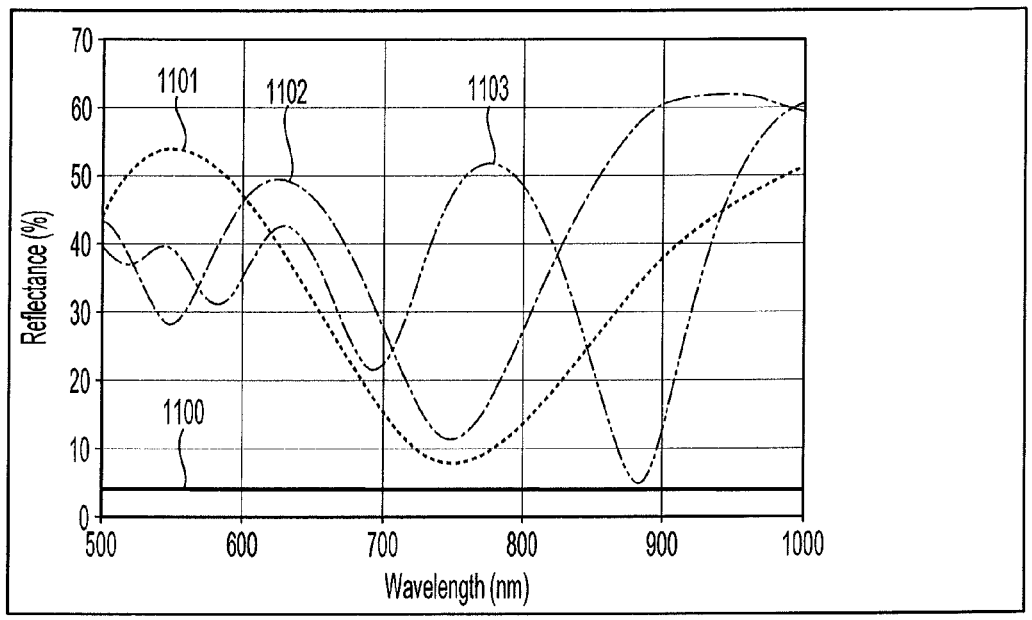
FIG. 11 shows several spectral scans (intermittent targets) from 500 nm to 1000 nm of a single GaAs thin film on glass substrate with thickness 365 nm.

In order to illustrate the operation of the system as described in FIG. 10, FIG. 11 provides spectral scans of the single GaAs thin film with 365 nm thickness 1103. The final curve gradually builds up, starting from the spectrum of the bare substrate 1100. Curves 1101 and 1102 correspond to the spectral curves when the physical thickness reaches 100 nm and 200 nm, respectively. For any given set of optical constants, the spectral scan is calculated and compared to the measured in real time spectral scan. In case the two curves coincide within reasonable tolerance, this is used to validate the new optical constant values, calculated from the time domain procedure. In case there is a difference, a small correction in the initial values of the optical constants is made and a new curve is generated until the theoretical and the measured curves coincide. This iterative correction and verification process can be performed in real time with certain frequency (for example 1-10 Hz). These calculations can continue back and forth between the time and the spectral domain until acceptable agreement between the optical constants in the two domains is achieved.

Figure 12:
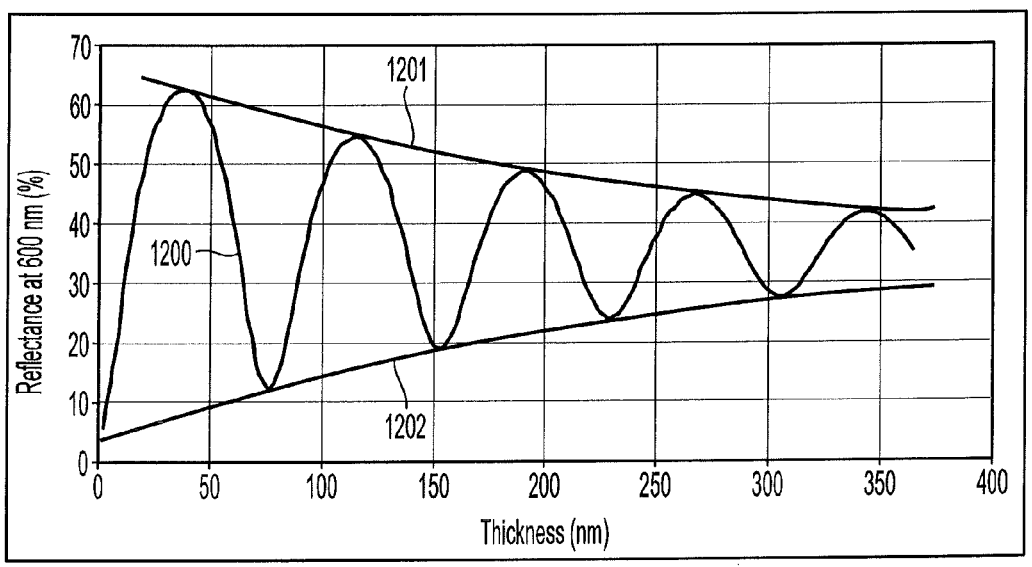
FIG. 12 is shows an example of optical monitoring function at 600 nm for the GaAs thin film with thickness 365 nm, shown in FIG. 11.

FIG. 12 shows the monitoring function in reflectance at 600 nm for the same GaAs thin film as depicted in FIG. 11. Due to the absorption of the material, the monitoring curve 1200 exhibits a typical attenuation, which allows calculation in real time of the extinction coefficient of the material. Curves 1201 and 1202 are the envelope curves, built by connecting the maxima 1201 and the minima 1202. Their shape can be used to predict the behavior of the film under deposition ahead of time (iterative prediction).

Typically, the measured values of the optical constants of most thin films are different than those assumed by the initial thin film design. Due to the fact that the thin film deposition process is far from physical equilibrium, the structure of the film is less bulky than the presumed one. In cases of materials with higher melting temperature than the deposition temperature, the films have specific columnar structure and pores (voids). Columnar structure/pores/cracks builds up when the impinging film particles cannot migrate efficiently to reach lower energetic states on the specimen surface and became frozen by the large flux on incoming particles. This case is specific for the deposition of solar cells, where the deposition rates are usually high. During this film deposition at high deposition rate, the films also come inhomogeneous with $\Delta n/n$ and $\Delta k/k$ changing with the film thickness. This effectively increases the film loss (absorption, scattering, etc.) and reduces the reflectance.

The packing density of the thin film is defined as the ratio between the density of the film and the density of the bulk material. There are several defined microstructures and associated with them structural models, such as Lorenz-Lorentz, Kinoshita-Nishobori, Chopra, volume averaging models and others, all of which are known to those skilled in the art. These and other models are applied to calculate the packing density of all or some of the thin films used in the thin film solar cells.

The columnar micro-structure creates local non-uniformity in the electric field within the film. The grain boundaries, contaminants, adsorbents, defects in the crystal structure effectively trap carriers and can dramatically reduce the efficiency of the photovoltaic device. As a result, the electrical properties of the photovoltaic structure are greatly dependent on local micro-mechanisms and always display the so called "size effect". This changes the minority carrier diffusion length and, therefore, the efficiency of the photovoltaic structure.

In case of lack of reasonably proven physical models, an empirical approach can be adopted where the measured optical and structural characteristics can be empirically related to the achieved solar cell efficiency. This approach seems takes into account the large diversity of thin film deposition technologies, which would be difficult to characterize with one unified physical model.

In one aspect, the system to accommodate or manage variability in production of surface modification process includes a monitoring mechanism to provide information to a control system that communicates with the production equipment. The communication from the control system may include information on a new deposition recipe, a required modification to the system parameters, combination of both, or a determination to reject if modifications will prove to be ineffective. Such a system could also be employed in other multilayer deposition process, or could be used in manufacturing where iterative modifications are likely.

A computer-readable medium having computer-executable instructions for control of a surface modification process which involves error detection and in real-time may also be produced. The instructions, when executed, performs the following steps: generating a product design/model based on a product specification; generating a first process recipe based on the product design/model; starting modification process of a specimen in a process chamber/module/equipment; monitoring one or more parameters of the specimen using one or more sensors; comparing monitored parameters with one or more target parameters; and deciding on whether to: (a) continue the process to an end point, (b) re-optimize the design model and modify the process recipe, or (c) reject the specimen.

Film deposition processes that may be used with one or more embodiments of the present invention are typically characterized in that they have a multi-layered deposition process. Aspects of the present disclosure can advantageously use an iterative re-optimization process to increase yield with tighter tolerances. Further, the methods and systems disclosed can add more predictability in the manufacturing process, thereby potentially reducing the necessity for manual supervision and human involvement. Examples of film deposition processes that may benefit from the re-optimizing control system include, but are not limited to, the solar panel production and liquid crystal display (LCD) thin film deposition.

Some embodiments of the present invention provide for design consideration for monitoring and communications implementation of such systems. Also, by automatic adjustment to the variation introduced in the manufacturing process, manual supervision is significantly reduced. Some embodiments involve collecting production information during the manufacturing process, calculating design path for the entire manufacturing process and allowable variances rather than at discrete layers, parameters, and communicating the information to the control system.

Several embodiments of the present disclosure are specifically illustrated and/or described herein. However, it will be appreciated that modifications and variations of the present disclosure are covered by the above teachings and within the purview of the appended claims without departing from the spirit and intended scope of the disclosure.

Figure 13:
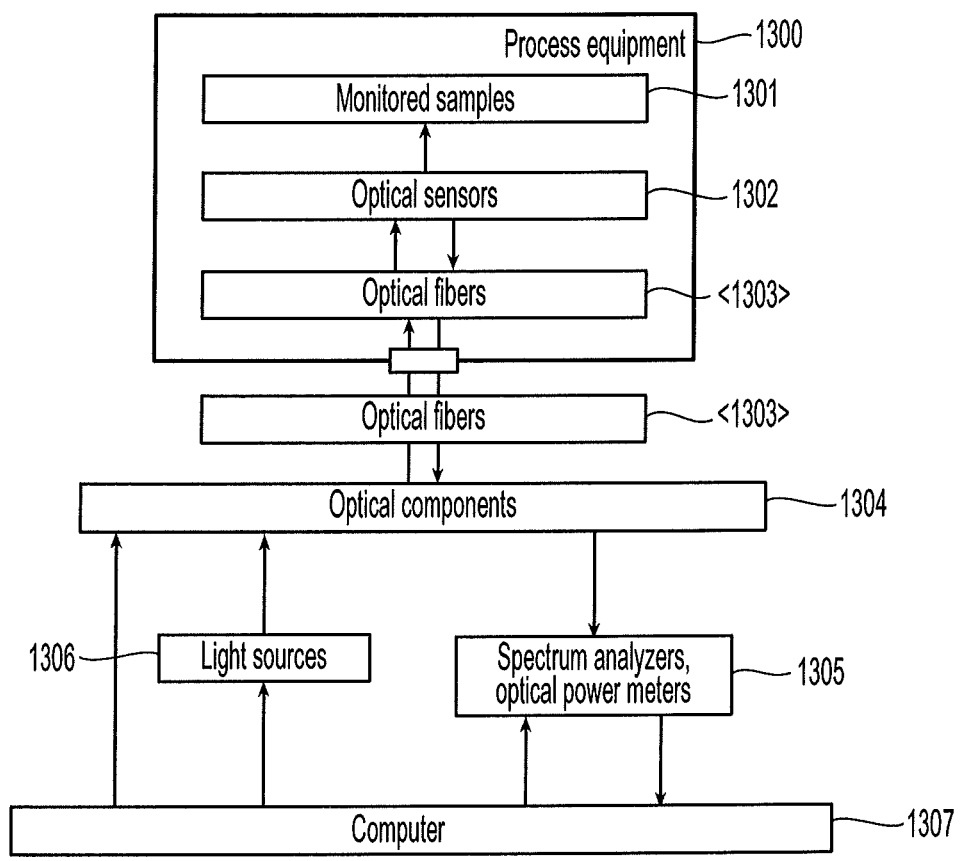
FIG. 13 shows a block diagram of a system for real time calculation of optical constants and other important film parameters in accordance with the present disclosure.

FIG. 13 shows a block diagram of a system according to one embodiment of the present invention. According to this embodiment, the monitoring optical sensors 1302 are installed inside the thin film process equipment 1300 by means of optical fibers 1303 in close proximity to the monitored sample/samples 1301. All other hardware components, such as other optical components (polarization control components, filters, isolators, etc.) 1304, light sources 1306, detectors, optical power meters, spectrum analyzers and spectrometers 1305, optical switches, computers 1306, etc. are located outside the process equipment and process the signal from the sensors.

Figure 14:
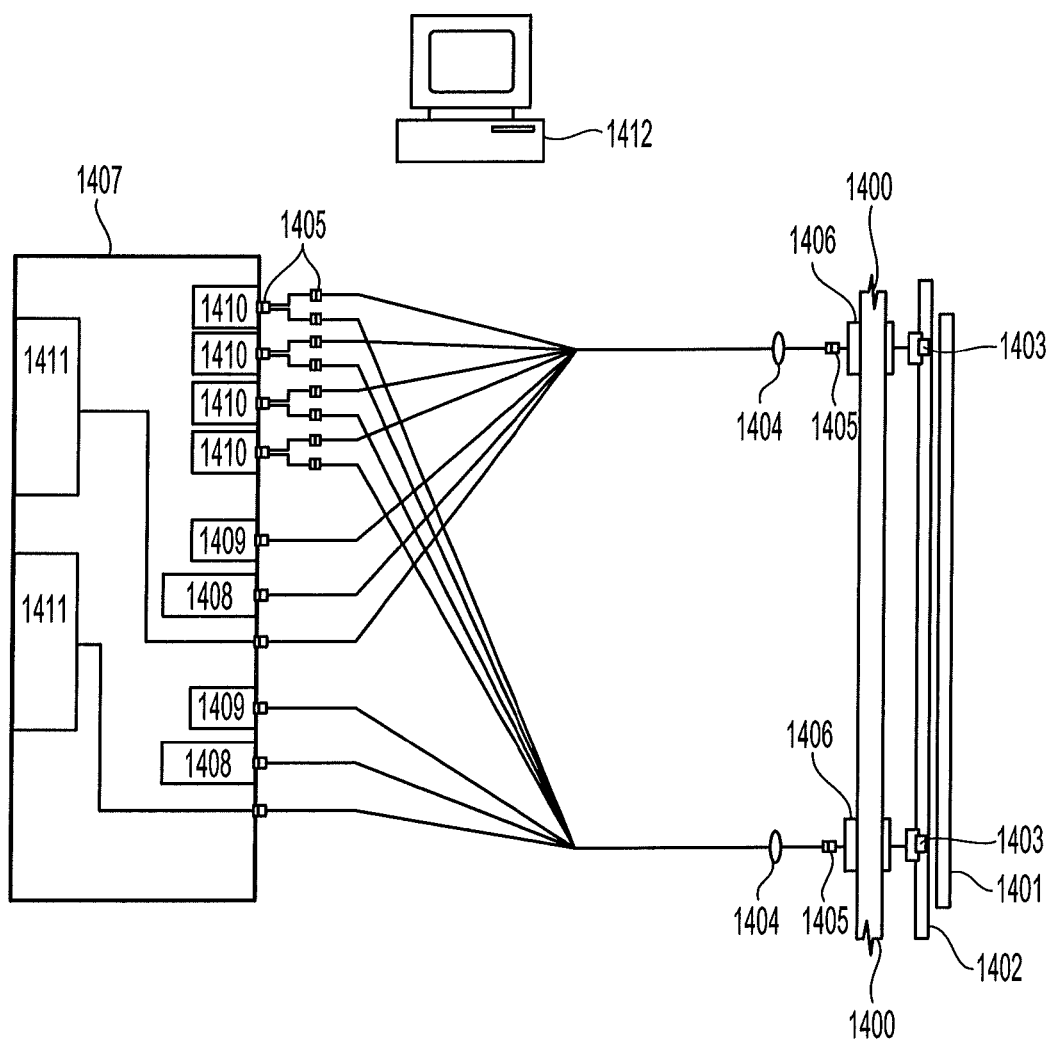
FIG. 14 shows a more detailed block diagram of a system in accordance with the present disclosure

FIG. 14 shows a detailed diagram of a system in accordance with one embodiment of the present invention. The monitoring system is installed in a vacuum chamber, which is represented by a wall 1400. The deposition substrate 1401 might be moving inside the chamber or might be stationary during the deposition. The monitoring of the substrate can take place either from the side where the film is deposited, or can take place from the opposite side (back side). The monitoring sensors 1403 are installed on the chamber component 1402. Only two sensors in a parallel configuration are shown. The chamber component 1402 can be any convenient component or device inside the chamber, such as the substrate heater or the deposition electrode or another component, or can be a specially designed mechanical fixture, holding the sensors in their position. The sensors are coupled to optical fibers 1404 by using fiber optics connectors 1405. All fibers are vacuum sealed and enter the vacuum chamber through specially designed feedthroughs 1406.

The hardware module 1407 holds the needed light sources, detectors and components. There are two laser sources 1408 at fixed wavelength. % and two optical power meters 1409, one for each of the two optical sensors. In this specific configuration there are also four white light LED sources 1410, which supply broadband light to each of the sensors and two optical spectrometers 1411, one for each of the sensors.

One of the white light LED sources supplies light to the sensors at normal incidence, while the remaining three LEDs supply light to the sensors at 3 different angles of incidence. The white light at normal incidence is reflected by the substrate and then is collected by the sensors and processed by the spectrometer to retrieve the spectral domain information. The incoming light at the different angles of incidence is reflected by the substrate and then collected by the sensor and processed by the spectrometer in order to measure the diffuse component of the reflectance and calculate haze. The LEDs work in sequence and are switched by the computer 1412. The computer 1412 controls the entire operations of the system, calculates the needed parameters, and stores the information.

The system as shown in FIG. 14 can operate as a standing alone system, but can also be connected to other similar systems positioned down the manufacturing line in a series configuration.

Figure 15:
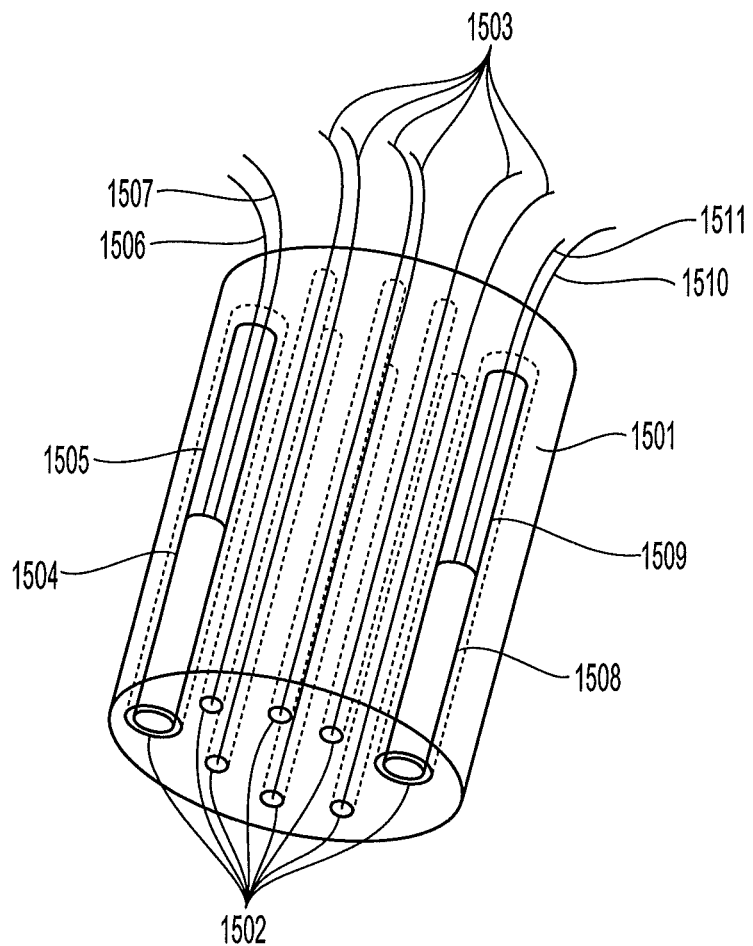
FIG. 15 shows an example of optical sensor for specular and diffuse reflectance in the time and spectral domains according to one aspect of the disclosure.

FIG. 15 shows an example of a novel optical sensor for detecting specular and diffuse reflectance in the time and spectral domains. The optical sensor comprises a solid body 1501 made of metal, ceramic, glass or other suitable material. There are a number of openings 1502 made through the solid body. The openings 1502 can have different diameters, different profiles or can be made at different angles in relation to the sensor face for collecting light at different angles. The openings are shown holding a variety of optical fibers 1503 and optical components. The fibers 1503 may be bare fibers or fibers with special metal or polymer cladding for handling high temperatures, fiber bundles, fiber optic collimators or other components assembled in variety of metal or other protective and/or alignment sleeves, etc.

Inside one of the openings 1502 may be a fiber optics collimator of the sort disclosed in aforementioned U.S. Pat. No. 6,879,744. Such a collimator may comprise a GRIN lens 1504, a dual fiber ferule 1505 and two fibers. A first single mode or multimode fiber 1506 may be used to deliver the incoming (laser) light and a second single mode or multimode fiber 1507 may be used for the collected light, reflected from the measured surface of the specimen. In this configuration, the described fiber optics collimator is used for measuring the specular reflectance at a fixed wavelength $\lambda_0$ (time domain).

Inside another of the openings 1502 may be a second fiber optics component used for measuring the specular reflectance within a spectral band $\Delta\lambda$ (spectral domain). It comprises an optical lens 1508, which in this example is shown as a GRIN lens, but could be any other type of optical lens or lens assembly (such as spherical, aspheric, duplet, triplet, GRADUIM lens), a fiber holder 1509 holding two multimode fibers, a first fiber 1510 for the incoming light and a second fiber 1511 for the collected specular reflectance. The fiber holder 1509 is shown as a dual fiber ferule, but could be any other holder designed for holding the two fibers in predetermined positions. The type of fibers used in the sensor could be also any type of single mode or multimode optical fibers of any material such as silica, sapphire, polymer, infrared material, etc.

In the example of FIG. 15, six large core multimode fibers 1503 are shown, which can be aligned at different angles, distances and positions towards the broadband light $\Delta\lambda$ in order to be able to illuminate or collect light from the illuminated surface at different angles and positions. As the film is deposited on the specimen, the diffuse reflectance (scattered light) from the film changes its spectral and angular distribution and is collected by the fibers 1503 for processing and calculation of optical haze and its angular distribution and used for calculation of the magnitude and type of surface roughness and other parameters described above.

The optical sensor described in FIG. 15 is designed to monitor thin film deposition on a solar panel or another flat panel or a flexible roll. The monitored substrate can constantly move or be stationary during the deposition. The sensor is designed to be installed in close proximity to the surface of the deposited film, usually at distance about 4-10 mm, depending on the type of film and configuration of the system. It can also be installed to monitor the film under deposition from the back side of the transparent substrate, which is beneficial for many superstrate manufacturing configurations and also prevents the sensor from being exposed to the deposition particles.

A plurality of such optical sensors can be installed inside the vacuum chamber or chamber compartments on a solar or other flat panel manufacturing line. They can be configured in parallel configuration to monitor film uniformity, parameter homogeneity and/or consistency of the deposition rate over the area of a panel, as the latter moves throughout the deposition equipment. They can be also configured in a series configuration along the manufacturing equipment to measure different deposition stages of the panel, different thin films or different etching or other surface modification stages. In addition, the optical sensors can be configured in a system where multiple sensors are installed both in parallel, and in series, along the manufacturing line and operated by the same control system.

It can be seen from the foregoing, that the present invention may find use in a variety of applications.

The present invention may find application in products which are manufactured, at least in part, by the removal of material (ablation), such as etching, grinding and so forth. The present invention may also find application in products which are manufactured, at least in part, by accretion of material by printing. The present invention may also find application in products which are manufactured, at least in part, by alternation of a material, such as by ion implantation.

It can be also seen from the foregoing that numerous processing and monitoring options are available, depending on the product being manufactured and the substrate being monitored.

With respect to the manufacture of thin films, a variety of processing options and monitoring options may be employed, and each of these may be used in different combinations. For example, monitoring may be performed in both the time and spectral domain, at one fixed wavelength and/or at least at one spectral range $\Delta\lambda$.

With respect to the manufacture of solar cells, a variety of processing options and monitoring options may be employed, and each of these may be used in different combinations. Monitoring can be done from the back side of the substrate. Both specular and diffuse reflection may be monitored. The material bandgap and surface roughness can be calculated in real time based on measured optical properties and their depth profiles. Different types of surface roughness may be calculated. The relative density and porosity may be calculated. Moving panels may be monitored in both parallel and in series sensor configuration. A real time surface map can be created for the moving panels, to show the uniformity (or non-uniformity) of one or more measured parameters across the panel surface. There can be iterative prediction of the specification to be met, and dynamic correction to ensure that the specification is better met. Differential signals may be taken from different sensors in parallel.

With respect to the design and deployment of sensors, a number of processing options and monitoring options may be available. The sensors may be configured to simultaneously monitor specular and diffuse reflectance or transmittance. The sensors may be configured to monitor at different angles of incidence. The sensors may be installed inside a processing chamber in close proximity to the surface being monitored. The sensors have an integrated sphere attached thereto. The sensor may include different configurations of fibers With respect to the manufacture of nanostructures, near-field scattering may be monitored. For photonic crystals and patterned coatings, the scattering may be measured from the back side of the substrate.

While the present invention has been described with reference to one or more specific embodiments, the description is intended to be illustrative as a whole and is not to be construed as limiting the invention to the embodiments shown. It is appreciated that various modifications may occur to those skilled in the art that, while not specifically shown herein, are nevertheless within the scope of the invention.

What is claimed is:

1. A computer-assisted method of making a product having a predetermined product specification and an initial product design which defines at least a partial structure of the product, the method comprising:
    (a) modifying a surface of a substrate to form an intermediate product;
    (b) measuring in real time, at least one measured parameter of said intermediate product;
    (c) comparing in real time, said at least one measured parameter with at least one target parameter;
    (d) in response to the result of the comparing step, employing a revised product design that is in accordance with the product specification;
    (e) continuing manufacture of the product based on the revised product design; and
    (f) repeating steps (a)-(e) until said predetermined product specification is reached;
    wherein steps (b)-(d) transpire as said surface continues to be modified and the product's product design is revised during the course of manufacture.

2. The method according to claim 1, comprising:
    calculating one or more secondary parameters from the at least one measured parameter.

3. The method according to claim 2, comprising:
    calculating a bandgap of the intermediate product.

4. The method according to claim 2, comprising:
    calculating a surface roughness of the intermediate product.

5. The method according to claim 1, comprising storing information about:
    a) the process parameters during the modification process;
    b) the equipment conditions during the modification process; and
    c) the surrounding environment condition during the modification process.

6. The method according to claim 5, comprising:
    calculating a product model based at least in part on the stored information and the at least one measured parameter.

7. The method according to claim 1, comprising:
    a) searching a database comprising product models during the modification process; and
    b) selecting a product model in response to said at least one measured parameter.

8. The method according to claim 1, wherein steps (b)-(e) are performed without disruption of the manufacturing process.

9. The method according to claim 1, wherein:
    said at least one measured parameter is an measured optical parameter; and
    said at least one target parameter is a target optical parameter.

10. The method according to claim 9, wherein:
    said at least one measured optical parameter is optical scattering.

11. The method according to claim 10, wherein:
    said at least one measured optical parameter is near field optical scattering.

12. The method according to claim 9, comprising:
    determining one or more of an angular range and an angular distribution of the measured optical parameter.

13. The method according to claim 9, comprising:
    determining one or more polarization components of the measured optical parameter.

14. The method according to claim 1, wherein:
    said at least one measured parameter is a uniformity measure of a physical parameter determined over a predetermined area of the specimen.

15. The method according to claim 1, wherein:
    said at least one measured parameter is a homogeneity measure of a physical parameter.

16. The method according to claim 1, comprising:
    taking a plurality of measurements in different chambers of a cluster tool during the course of making said product; or taking a plurality of measurements in different compartments of a chamber during the course of making said product, or
both.

17. The method according to claim 1, comprising:
measuring said at least one parameter at one or more fixed wavelengths.

18. The method according to claim 1, comprising:
measuring said at least one parameter in one or more predetermined continuous spectral ranges.

19. The method according to claim 1, comprising:
measuring said at least one parameter simultaneously at fixed wavelengths and within predetermined spectral ranges; and
comparing the measured values with their target values both at said fixed wavelengths and said predetermined spectral ranges.

20. The method according to claim 1, comprising
taking a plurality of different measured parameters of said intermediate product; and
comparing said plurality of different measured parameters with a corresponding plurality of target parameters, before revising said initial product design.

21. The method according to claim 1, comprising:
if a current value of said at least one measured parameter is sufficiently close to a previous value for the same at least one measured parameter, using a previously revised initial product design, instead of revising the initial product design based on current results of the comparing step.

22. The method according to claim 1, further comprising:
performing one or more of iterative prediction and iterative calculation; and
verifying and validating the resulting prediction and/or calculation.

23. The method according to claim 1, further comprising:
monitoring at least one finite band of wavelengths to form a measured spectral scan; and
monitoring at least one reference wavelength to form said at least one measured parameter, wherein:
said at least one measured parameter comprises at least one measured optical parameter.

24. The method according to claim 23, comprising:
based at least in part on said at least one measured optical parameter, forming a predicted spectral scan on the assumption that a particular physical property has changed;
comparing the predicted spectral scan with the measured spectral scan to form at least one spectral difference metric;
based at least in part on said at least one spectral difference metric, verifying that said physical property has changed.

25. The method according to claim 1, wherein the at least one measured parameter is one from the group consisting of:
transmission of one or more specified wavelengths, reflection of one or more specified wavelengths, thickness, deposition rate, polarization, refractive index, absorption, scattering, photo-luminescence, an electro-optical parameter, an acousto-optical parameter and a thermo-optical parameter.

26. A processing system configured to make a product having a predetermined product specification and an initial product design which defines at least a partial structure of the product, the processing system comprising:
(a) at least one processing apparatus configured to accommodate a substrate having a surface to be modified in order to form an intermediate product;
(b) at least one detector for measuring, in real time, at least one measured parameter of said intermediate product; and
(c) one or more computers programmed to:
(c1) compare, in real time, said at least one measured parameter with at least one target parameter derived from the initial product design;
(c2) create a revised product design that is in accordance with the product specification, based at least in part on the result of comparing the at least one measured parameter with the at least one target parameter derived from the initial product design;
(c3) store information reflective of the revised product design; and
(c4) control the processing chamber so that it continues manufacture the product based on the revised product design,
while a surface of said intermediate product continues to be modified; and
wherein the product's product design is revised during the course of manufacture.

27. The processing system according to claim 26, wherein:
the one or more computers are further programmed to decide, based on the outcome of comparing in real time, whether to:
(d1) continue the process to an end point;
(d2) re-optimize the design model and/or modify the process recipe, or
(d3) reject the intermediate product.

28. The processing system according to claim 26, wherein:
the detector comprises an optical device.

29. The processing system according to claim 28, wherein:
the detector comprises a fiber optics device.

30. The processing system according to claim 29, wherein the fiber optics device comprises:
a) single mode optical fibers and components; and also
b) multimode optical fibers and components.

31. The processing system according to claim 30, wherein:
the single mode and multimode optical fibers and components are positioned at different distances and angles, relative to a measured surface of the intermediate product.

32. The processing system according to claim 30, wherein:
a plurality of illumination fibers are included among the single mode optical fibers and multimode optical fibers; and
the illumination fibers are positioned to transmit light at different distances and angles of incidence, relative to a measured surface of the intermediate product.

33. The processing system according to claim 26, wherein:
the detector is configured to measure the at least one measured parameter from the back side of the intermediate product.

34. The processing system according to claim 26, wherein:
a plurality of detectors are provided; and
the plurality of detectors are positioned to monitor different areas of a single intermediate product.

35. The processing system according to claim 26, wherein:
a plurality of detectors are provided; and
the plurality of detectors are positioned to monitor different intermediate product.

36. The processing system according to claim 26, wherein:
a plurality of detectors are provided; and
the plurality of detectors are positioned to monitor different stages of modification of the same intermediate product.

37. The processing system according to claim 26, wherein:
a plurality of detectors are provided; and
the plurality of detectors are positioned at close proximity to a surface of the intermediate product to detect scattered light from the intermediate product.

38. The method according to claim 1, comprising making at least one of: a solar cell, a flat screen monitor, a semiconductor, an optical thin film, a nanostructured 2D or 3D device, and a printed product.

39. The method according to claim 6, wherein the product model comprises:
a detailed product description including its design and structure.

40. The method according to claim 39, wherein the product model comprises at least one or more of:
a mathematical relationship;
a data collection in numerical form; and
a data collection in graphical form.

41. The method according to claim 40, wherein the product model comprises:
a graphical representation of a mathematical relationship.

42. The method according to claim 14 wherein:
the physical parameter whose uniformity is measured, is a thickness of the intermediate product.

43. The method according to claim 15 wherein:
the physical parameter whose homogeneity is measured, is a chemical composition of the intermediate product.

44. The method according to claim 25, comprising:
measuring at least one of a transmission and a reflection at one or more wavelengths; and
determining a drift in a spectral peak of said transmission and/or reflection.

* * * * *